United States Patent
Berkow

(10) Patent No.: US 8,423,108 B2
(45) Date of Patent: Apr. 16, 2013

(54) DEVICE AND SYSTEM THAT IDENTIFIES CARDIOVASCULAR INSUFFICIENCY

(75) Inventor: Jan Berkow, Allison Park, PA (US)

(73) Assignee: Intelomed, Inc., Allison Park, PA (US)

(*) Notice: Subject to any disclaimer, the term of this patent is extended or adjusted under 35 U.S.C. 154(b) by 316 days.

(21) Appl. No.: 12/723,913

(22) Filed: Mar. 15, 2010

(65) Prior Publication Data
US 2011/0152651 A1    Jun. 23, 2011

Related U.S. Application Data

(63) Continuation-in-part of application No. 11/388,661, filed on Mar. 24, 2006, now Pat. No. 7,678, 057.

(60) Provisional application No. 60/664,896, filed on Mar. 24, 2005.

(51) Int. Cl.
*A61B 5/00* (2006.01)

(52) U.S. Cl.
USPC ............................ 600/324; 600/481; 600/484

(58) Field of Classification Search .................. 600/309, 600/310, 322–324, 481, 484, 485, 500, 501–502, 600/504, 507
See application file for complete search history.

(56) References Cited

U.S. PATENT DOCUMENTS

| | | | |
|---|---|---|---|
| 5,830,131 A | 11/1998 | Caro et al. | |
| 5,865,756 A * | 2/1999 | Peel, III | 600/490 |
| 6,485,431 B1 | 11/2002 | Campbell | |
| 6,575,912 B1 | 6/2003 | Turcott | |
| 6,719,705 B2 | 4/2004 | Mills | |
| 6,776,764 B2 | 8/2004 | Pinsky | |
| 6,858,006 B2 | 2/2005 | MacCarter et al. | |
| 7,044,918 B2 * | 5/2006 | Diab | 600/502 |
| 7,285,090 B2 | 10/2007 | Stivoric et al. | |
| 7,324,848 B1 * | 1/2008 | Turcott | 607/17 |
| 7,328,053 B1 | 2/2008 | Diab et al. | |
| 7,330,750 B2 | 2/2008 | Erkkila et al. | |
| 2005/0197675 A1 | 9/2005 | David et al. | |
| 2006/0293384 A1 | 12/2006 | Whewell | |
| 2008/0255471 A1 | 10/2008 | Naghavi et al. | |

FOREIGN PATENT DOCUMENTS

| WO | 03/077854 | 9/2003 |
|---|---|---|
| WO | 2005/107584 | 11/2005 |

OTHER PUBLICATIONS

Feissel, M. et al., "Respiratory Variaton of Plethysmography Signal with a Pulse Oximeter: New Predictive Parameters of Fluid Responsiveness?", Proceedings of the American Thoracic Society, vol. 3, Apr. 2006, A.295.

Ridel, C. et al., "Prediction of Fluid Responsiveness in Spontaneously Breathing Patients: Response to Passive Leg Raising Measured by Pulse Contour Cardiac Output", Proceedings of the American Thoracic Society, vol. 3, Apr. 2006, A.295.

Kim, H.K. et al., "Can Cardiac Contractility be Estimated by an Inspiratory Hold Maneuver?", Proceedings of the American Thoracic Society, vol. 3, Apr. 2006, A.296.

(Continued)

*Primary Examiner* — Patricia Mallari
*Assistant Examiner* — Michael D'Angelo
(74) *Attorney, Agent, or Firm* — Alicia M. Passerin, Esq.; Pietragallo Gordon Alfano Bosick & Raspanti, LLP

(57) ABSTRACT

A system and method for identifying volume status of a patient are disclosed. A pulse density signal is recorded from the patient. The pulse density signal is filtered to capture a respiration sampling period and a plurality of cardiac cycles occurring during the respiration sampling period. Mean pulse pressure and peak blood flow velocity for the respiration sampling period are calculated and are used as indices of volume status of the patient.

25 Claims, 17 Drawing Sheets

OTHER PUBLICATIONS

Lamia, B. et al., "Brachial Pulse Pressure is Related to Total Arterial Compliance and Stroke Volume in ICU Patients: An Arterial Tonometric Study", Proceedings of the American Thoracic Society, vol. 3, Apr. 2006, A.296.

Monnet, X. et al., "Measuring Aortic Diameter is Essential for Assessing Fluid Challenge by Esophageal Dopppler", Proceedings of the American Thoracic Society, vol. 3, Apr. 2006, A.296.

Zamanian, M. et al., "Assessment of Cardiac Function and Ventilatory Efficiency by Noninvasive CO2 Monitoring during Reduction of Ventilatory Support in Patients with CHF", Proceedings of the American Thoracic Society, vol. 3, Apr. 2006, A.297.

Kim, H.K. et al., "Determinates of Arterial Pulse Pressure and Stroke Volume Variation during Positive-Pressure Ventilation", Proceedings of the American Thoracic Society, vol. 3, Apr. 2006, A.297.

* cited by examiner

US 8,423,108 B2

DEVICE AND SYSTEM THAT IDENTIFIES CARDIOVASCULAR INSUFFICIENCY

CLAIM OF PRIORITY

This application is a continuation-in part of U.S. patent application Ser. No. 11/388,661, filed on Mar. 24, 2006, now U.S. Pat. No. 7,678,057, which claims the benefit of U.S. Provisional Patent Application Ser. No. 60/664,896, filed on Mar. 24, 2005.

BACKGROUND

Despite the development of regional trauma centers, improved emergency transport systems to reduce the total time in shock, and aggressive resuscitation treatments, trauma patient mortality and morbidity remains high. Traumatic injury is the leading cause of death in subjects <44 years of age, resulting in over 150,000 deaths annually. Severe hypovolemia due to hemorrhage is a major factor in nearly half of those deaths. Furthermore, patients who survive the initial injury are at a high risk of developing subsequent multiple organ dysfunction syndrome and sepsis with a significant rate of late mortality in the ICU. More effective patient monitoring technology would identify patients at risk to develop organ failure and guide appropriate therapy.

Current monitoring required to assess hemodynamic function is often invasive and is limited to high acuity settings. Non-invasive monitoring conducive to lower acuity settings (i.e., areas of care where invasive and cumbersome monitoring techniques cannot be practically implemented) currently provides static, unidimensional, and isolated information of questionable utility.

Severe shock associated with trauma is characterized by a decreased circulatory blood flow that does not meet the metabolic demands of the body. Shock is the result of a vast array of processes with different time courses, degrees of cardiovascular compensation, monitoring needs, pathophysiologies, treatments, and outcomes. However, in all cases, prolonged and unrecognized impaired tissue perfusion will cause organ injury, increased morbidity, and death. Circulatory shock occurs from any of a variety of causes, but has as its hallmark inadequate tissue perfusion such that ischemic dysfunction and organ injury inevitably develop. If tissue hypoperfusion is not reversed by intravascular fluid resuscitation and/or pharmacologic support aimed at restoring normal cardiac performance and vasomotor tone, organ failure and death occur. However, only half of the patients with cardiovascular insufficiency increase their cardiac output in response to volume loading. Thus, it is important to identify which patients are preload-responsive (i.e. they will increase their cardiac output in response to fluid resuscitation) because giving fluid resuscitation to a patient who is not preload-responsive will not improve their circulatory status and delays effective treatment. Delaying treatment results in organ injury and intravascular volume overload, which induces acute right ventricular failure (acute cor pulmonale) and pulmonary edema, both of which can compromise normal homeostatic mechanisms and induce circulatory shock and death.

The prior art has at least three major deficiencies. First, the devices available to monitor a patient's systemic stability are quite insensitive. Second, the mechanisms for monitoring such patients requires that patients are either mechanically ventilated or are in an environment in which only crude maneuvers may be implemented to perturb the cardiovascular system, such as by raising a leg or abdominal compressions. Finally, the output generated by currently available devices requires skilled care providers to interpret the output and to decide appropriate actions or treatment protocols.

Thus, there is a need for a device that can transform insensitive signals into something meaningfully related to the subject's systemic state. There is also a need for a method that can be implemented in a spontaneously breathing subject and/or avoids the inconvenience of physical maneuvers to perturb the cardiovascular system. Finally, there is a need for a device that can be used by a less skilled care provider, such as emergency response personnel, so that critically ill patients receive effective treatment quickly.

SUMMARY

A method for identifying volume status of a patient is disclosed. The method comprises the steps of recording a pulse density signal from the patient and filtering the pulse density signal to capture a respiration sampling period and a plurality of cardiac cycles occurring during the respiration sampling period. A mean pulse pressure for the respiration sampling period is calculated using a computer as the quotient of the sum of the pulse pressure for each cardiac cycle occurring during the respiration sampling period to the total number of cardiac cycles occurring during the respiration sampling period. Optionally, a peak blood flow velocity is calculated as a difference between the mean minimum pressure for the respiration sampling period and a mean pulse pressure for the respiration sampling period. The mean pulse pressure and peak blood flow velocity are used as indices of volume status of the patient. In examples, changes in mean pulse pressure and peak blood flow velocity between first and second respiration sampling periods in response to a cardiovascular pre-load are classified and translated to identify a volume status of the patient.

A system for identifying volume status of a patient is also disclosed. In an embodiment, the system comprises a sensor that records a pulse density signal from the patient. A controller controls the sensor to initiate a record of the pulse density signal. A processor is configured to filter the pulse density signal to capture a respiration sampling period and filter the pulse density signal to capture a respiration sampling period and a plurality of cardiac cycles occurring during the respiration sampling period. The processor is also configured to calculate a mean pulse pressure for the respiration sampling period as the quotient of the sum of the pulse pressure for each cardiac cycle occurring during the respiration sampling period to the total number of cardiac cycles occurring during the respiration sampling period. Optionally, the processor is also configured to calculate a peak blood flow velocity, which is calculated as a difference between the mean minimum pressure for the respiration sampling period and a mean pulse pressure for the respiration sampling period. Mean pulse pressure and peak blood flow velocity are used as indices of volume status of the patient. Optionally, changes in mean pulse pressure and peak blood flow velocity between first and second respiration sampling periods are classified and translated to identify a volume status of the patient.

In another embodiment, the system comprises a sensor that records a pulse density signal from the patient. A controller controls the sensor to initiate the record of the pulse density signal. A signal conditioning module comprises an amplifier that amplifies the pulse density signal and a converter that converts the amplified signal to a digital signal. The signal conditioning module transmits the converted, amplified signal to a signal processing module. The signal processing module is configured to filter the signal to capture a respiration sampling period and a plurality of cardiac cycles occurring during the respiration sampling period. The signal processing module also calculates a mean pulse pressure for the respiration sampling period as the quotient of the sum of the pulse pressure for each cardiac cycle occurring during the respiration sampling period to the total number of cardiac cycles occurring during the respiration sampling period. The signal processing module is also configured to calculate a peak blood flow velocity as a difference between the mean minimum pressure for the respiration sampling period and a mean pulse pressure for the respiration sampling period. Optionally, mean pulse pressure and peak blood flow velocity are used as indices of volume status of the patient. Optionally, a pattern recognition module is configured to calculate changes in mean pulse pressure and peak blood flow velocity between first and second respiration sampling periods which are classified and translated to identify a volume status of the patient.

A non-invasive apparatus for use to identify volume status of a patient is also disclosed. The device comprises means for recording a pulse density signal from the patient and means for filtering the pulse density signal to capture a respiration sampling period and a plurality of cardiac cycles occurring during the respiration sampling period. There is also means for calculating a mean pulse pressure for the respiration sampling period, wherein the mean pulse pressure is the quotient of the sum of the pulse pressure for each cardiac cycle occurring during the respiration sampling period to the total number of cardiac cycles occurring during the respiration sampling period. There is also means for calculating a peak blood flow velocity as a difference between the mean minimum pressure for the respiration sampling period and a mean pulse pressure for the respiration sampling period. Mean pulse pressure and peak blood flow velocity are used as indices of volume status of the patient. Optionally, there is also means for calculating changes in mean pulse pressure and peak blood flow velocity between first and second respiration sampling periods which are classified and translated to identify a volume status of the patient.

A computer-readable medium is also disclosed. Instructions cause the processor to calculate a mean pulse pressure for a respiration sampling period, wherein the mean pulse pressure is the quotient of the sum of the pulse pressure for each cardiac cycle occurring during the respiration sampling period to the total number of cardiac cycles occurring during the respiration sampling period. Instructions also cause the processor to calculate a peak blood flow velocity as a difference between the mean minimum pressure for the respiration sampling period and a mean pulse pressure for the respiration sampling period. Mean pulse pressure and peak blood flow velocity are used as indices of volume status of the patient. Optionally, changes in mean pulse pressure and peak blood flow velocity between first and second respiration sampling periods are classified and translated to identify a volume status of the patient.

These and other details, objects, and advantages of the disclosed system and method will become better understood or apparent from the following descriptions, examples, and figures showing embodiments thereof.

DETAILED DESCRIPTION

Figure 1A:
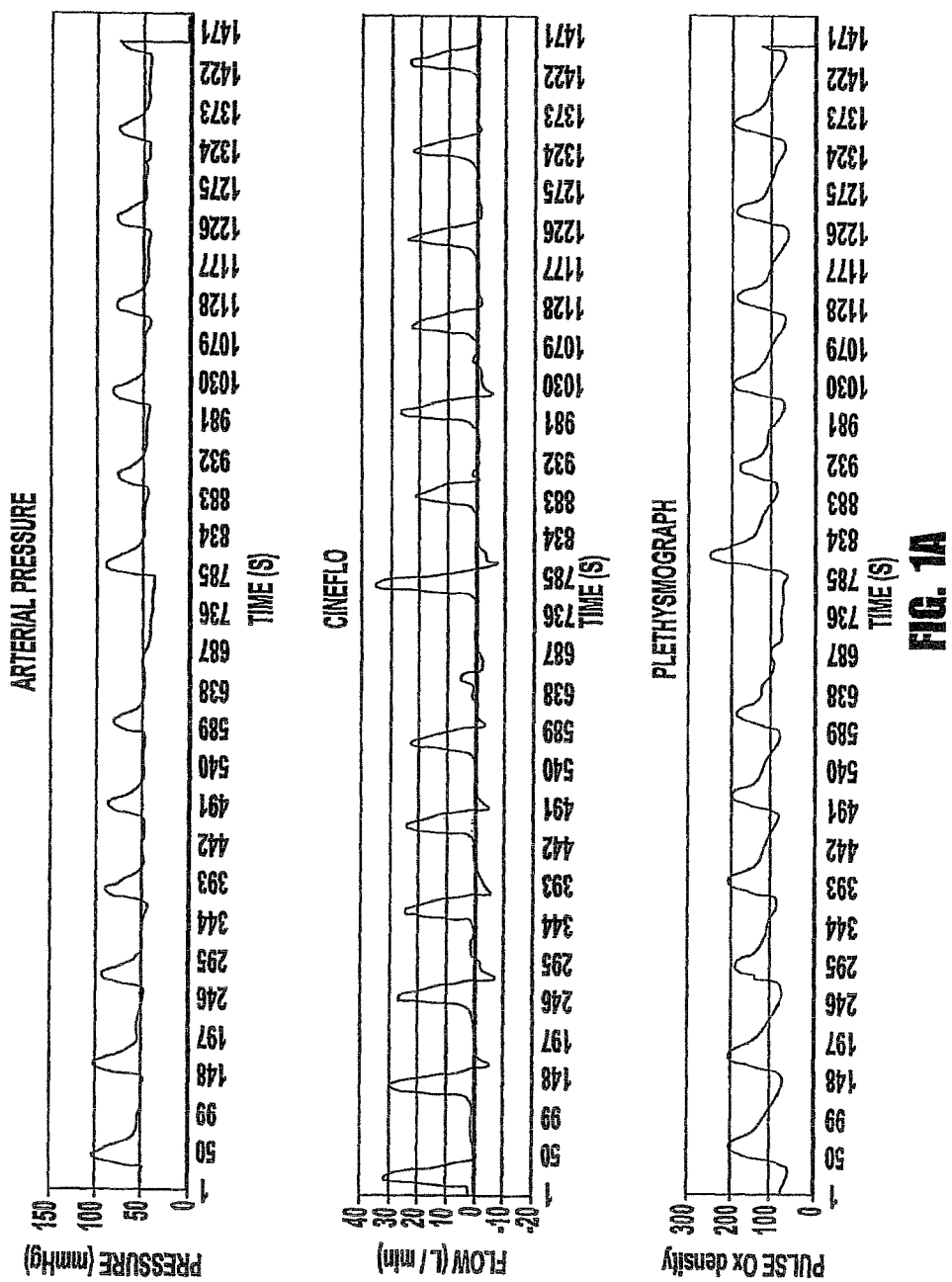
FIG. 1A shows strip chart recordings of arterial pressure, aortic flow, and pulse oximeter density during positive pressure ventilation.

The pulse density signal generated by a photoplethysmograph such as from the near infrared channel of a pulse oximeter correlates with the pulsatile changes in arterial blood pressure in the same subject. This relationship is illustrated in FIG. 1A. The top chart recording is an arterial pressure trace, the middle chart recording shows aortic flow, and the bottom chart recording shows pulse density from a pulse oximeter. These data were collected from a subject undergoing coronary bypass surgery. The arterial pressure data were obtained using a femoral artery catheter and aortic flow data were obtained using a Cineflo® electromagnetic flow meter, with the flow probe positioned in the aorta. These graphs are shown to depict the strong correlation between the beat-to-beat variations in flow and arterial pressure compared to the variation in pulse density recorded from a photoplethysmograph.

Figure 1B:
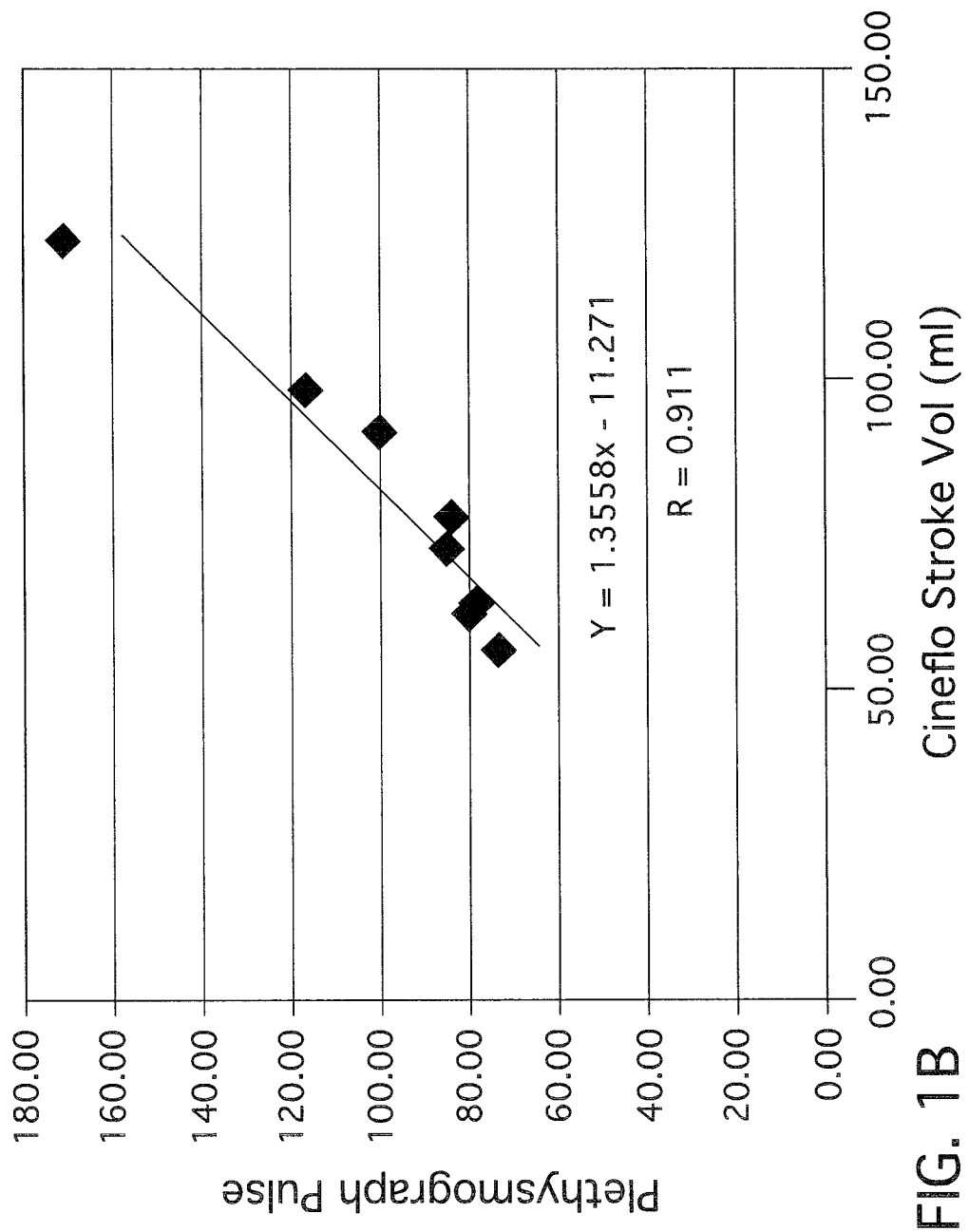
FIG. 1B shows that the pulse pressure variation signal obtained from a photoplethysmograph is significantly correlated with a measure of stroke volume variation obtained from an aortic probe.

FIG. 1B shows a graph that illustrates the significant correlation between the pulse pressure variation signal obtained from a photoplethysmograph and stroke volume as measured by a Cineflo® flow probe.

Figure 6:
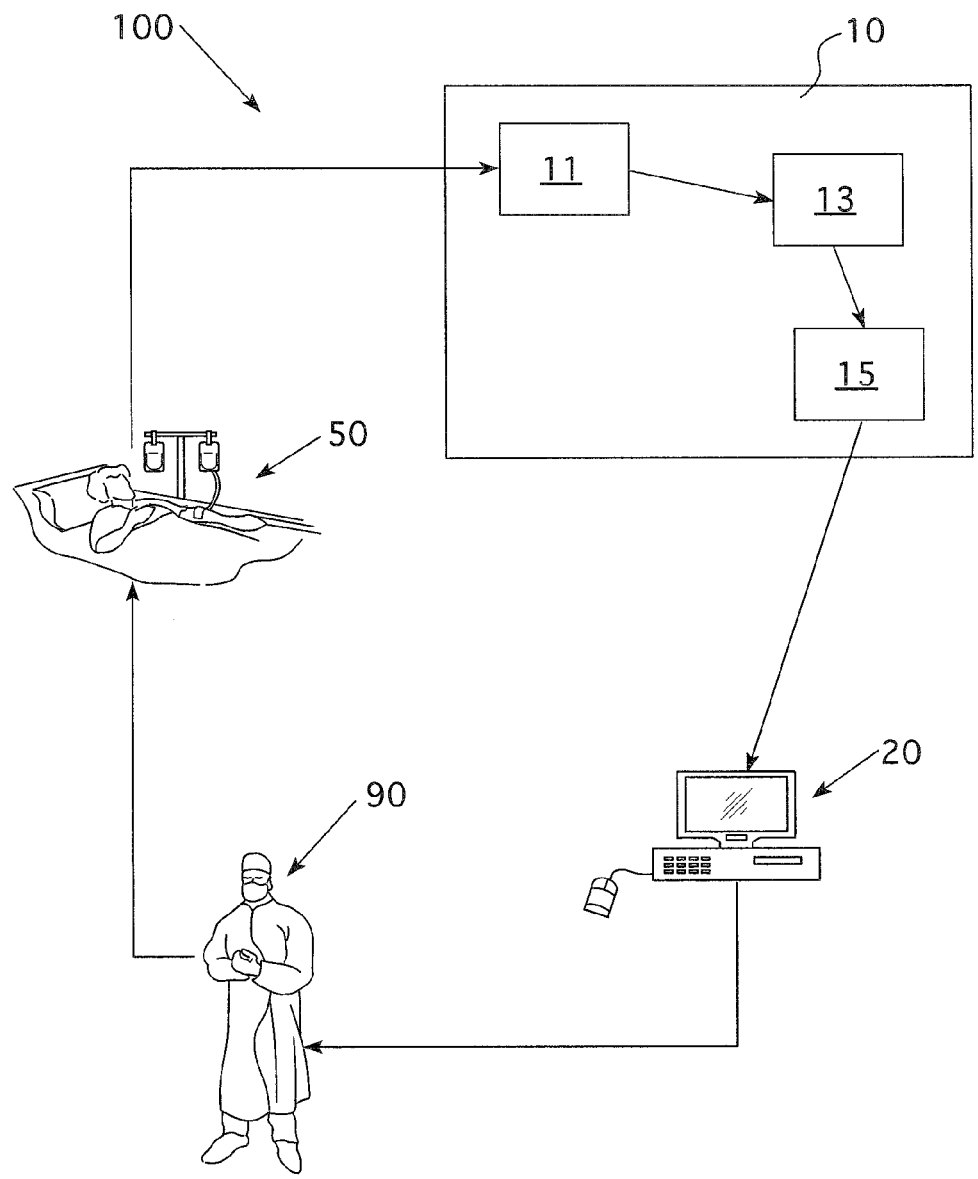
FIG. 6 shows a schematic of an example of a claimed system.
Figure 8:
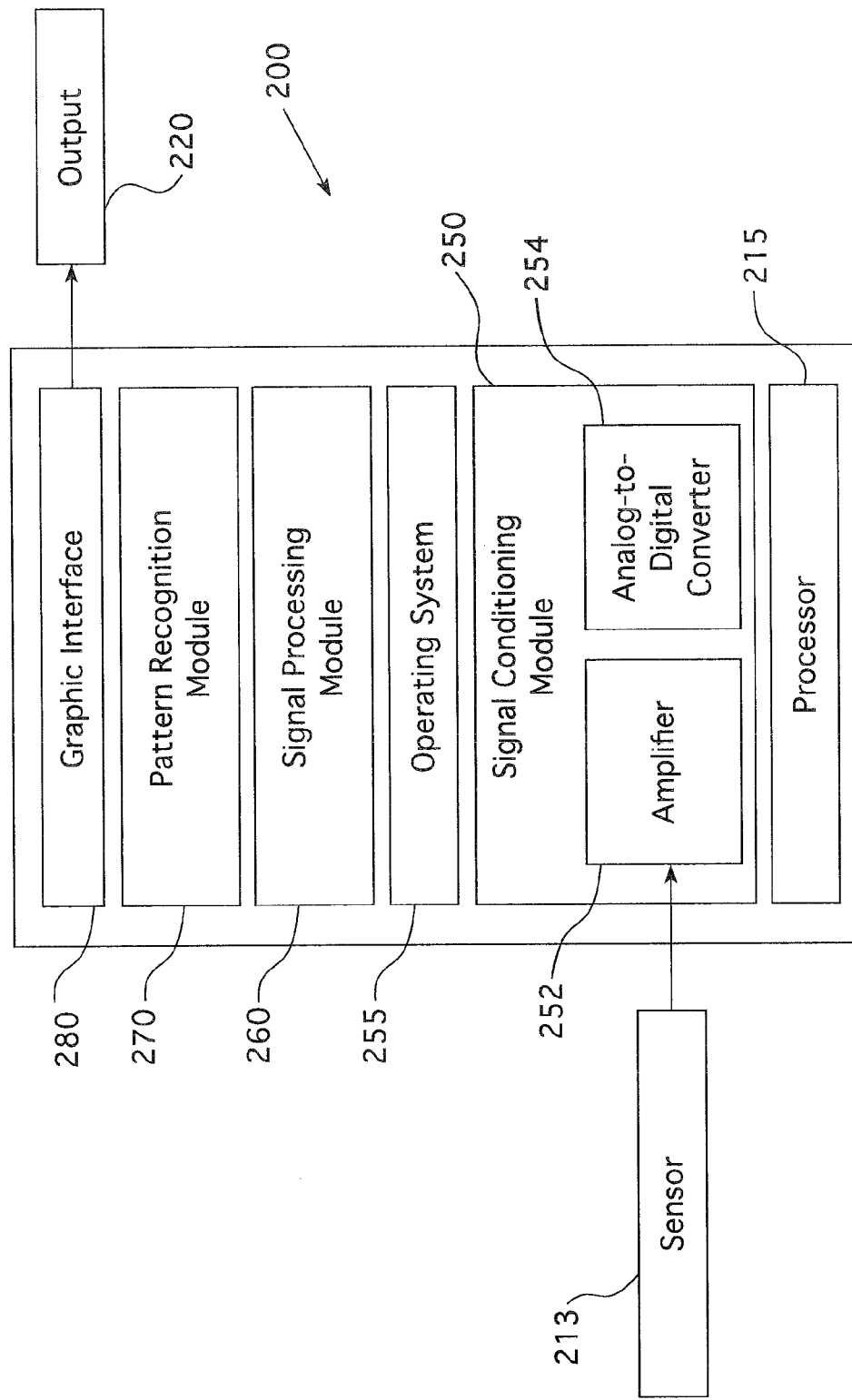
FIG. 8 shows a schematic of a second embodiment of a system for identifying volume status.

Embodiments of the claimed systems 100, 200 are shown in FIGS. 6 and 8, respectively. In the embodiment shown in FIG. 6, the system 100 is a computer system, although the system may be implemented in any combination of hardware and software, as long as the combination does not interfere with the scope and intended use of the claimed system. In an example, the system comprises a subject 50, a device 10 such as the one described above, and a healthcare provider 90, researcher, or leader, such as a lead fire-fighter or a military superior. The device has a storage medium that stores instructions (not shown), a controller 11 that initiates data collection from the subject, a sensor 13 that collects and transfers data, and a processor 15 unit that reduces the data and uses the instructions to carry out at least one of a plurality of steps. In an example, the instructions carry out at least one of the steps of initiating the controller 11 to collect data, instructing the sensor 13 to collect data and transfer a data signal, perturbing the subject 50, processing the data into at least one output 20, analyzing the output 20, displaying the output 20, or deciding how to use the output 20. In an example, the healthcare provider 90 or researcher review the output and/or use the output to institute a treatment protocol, such as where the subject is cardiovascularly insufficient or hypovolemic. In other examples, the healthcare provider monitors or manages the subject 50, for example, from a remote location, as described above.

The processor 15, 215 may contain a single microprocessor, or may contain a plurality of microprocessors for configuring the computer as a multi-processor system. The storage medium, or main memory, stores in part instructions and data for execution by the processor unit. If the method is implemented in software, the main memory stores the executable code when in operation. The main memory may be in the form of dynamic random access memory or any storage medium known in the art.

Figure 9:
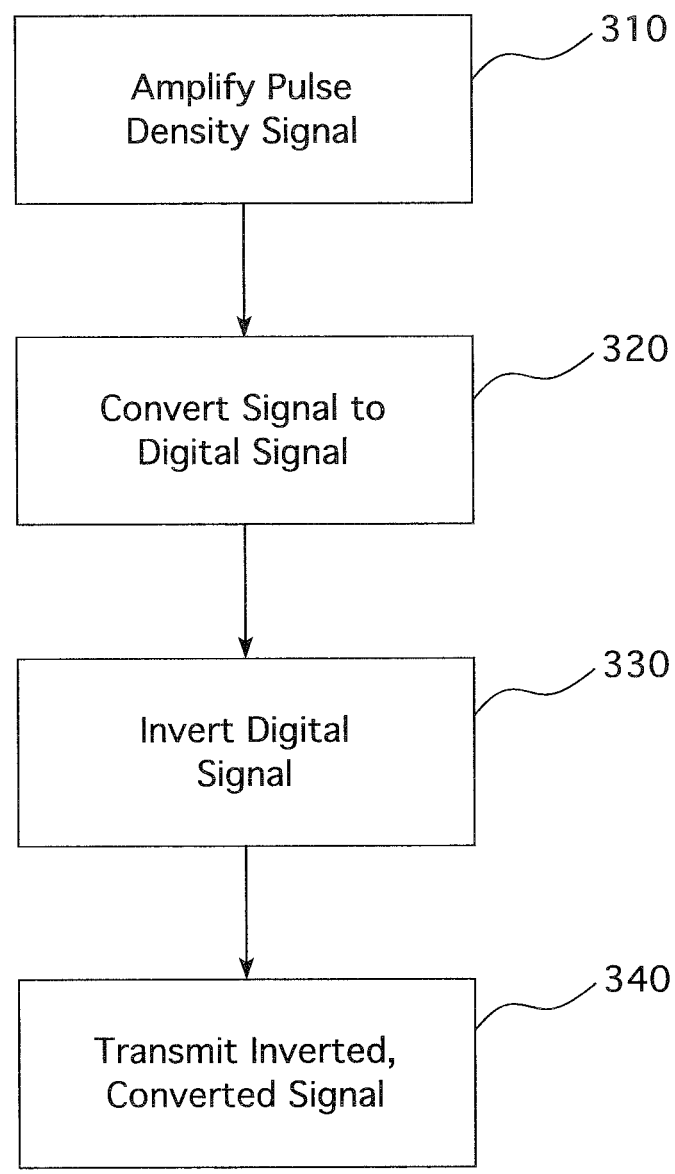
FIG. 9 shows a flow diagram outlining the steps performed by the signal conditioning module.
Figure 10:
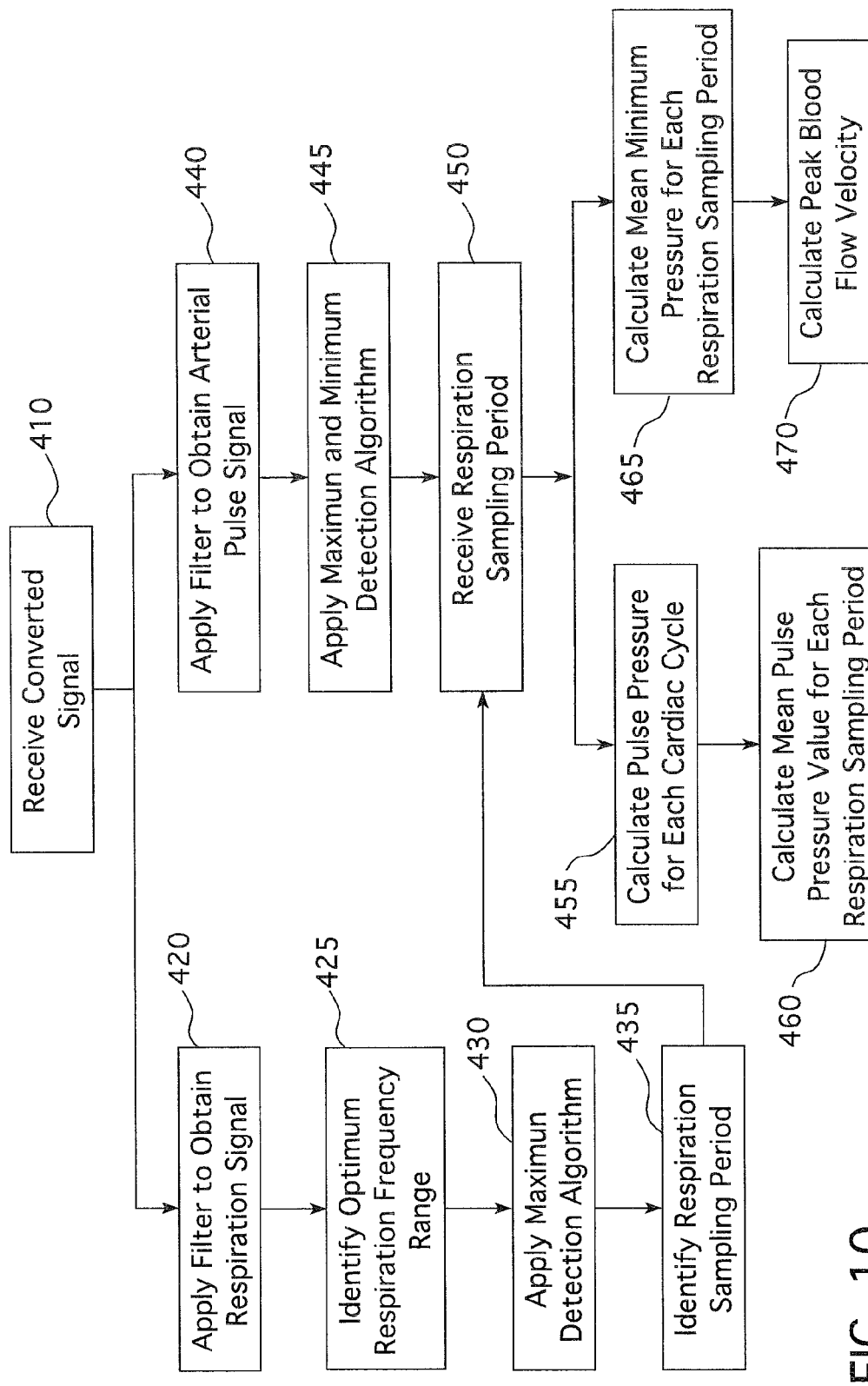
FIG. 10 shows a flow diagram outlining the steps performed by the signal processing module.

A data signal is transferred to the processor 15, 215 by the sensor 13, 213, such as for example a photoplethysmograph, that supplies data regarding a physiological condition of the subject. In an embodiment, the processor 15 reduces the data and uses instructions (not shown) to carry out at least one of the steps of the claimed method, shown in FIG. 4 and described in detail below. In another embodiment, the processor 215 reduces the data and uses instructions (not shown) to carryout out at least one of the steps of the claimed method, shown in FIGS. 9-11 and described in detail below. These steps generate an output 20, 220. Output 20, 220 may be any output that a researcher 90 or a healthcare provider uses to either identify, treat, manage, or monitor a subject. Output 20, 220 includes at least the examples described below but may be in any form that could be used in a clinical or research setting.

The sensor 13 provides a portion of the user interface for a user of the computer system. The components contained in the computer system are those typically found in general purpose computer systems, and in fact, these components are intended to represent a broad category of such computer components that are well known in the art.

Figure 12B:
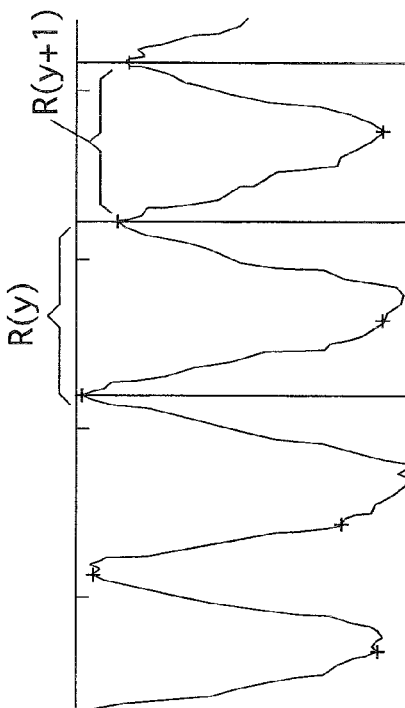
FIG. 12B shows the pulse density signal of FIG. 12A filtered to capture a plurality of respiration sampling periods.
Figure 12A:
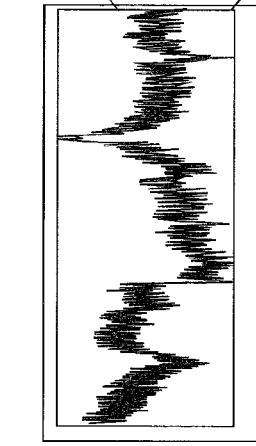
FIG. 12A shows an unfiltered pulse density signal recorded by a photoplethysmograph.

Another embodiment of the system 200 is shown in FIG. 8. The system 200 has a sensor 213 that records a pulse density signal from the patient. The recording is either continuous or continuously intermittent. In an example, the sensor 213 is a photoplethysmograph, which is a device that operates by capturing changes in light absorption affected primarily by pulsatile blood density. In examples where the sensor 213 is a photoplethysmograph, the sensor 213 is either a dedicated optical sensor that operates in the near infrared frequency range or may be a near infrared sensor that is shared by another device such as the use of a near infrared channel of a pulse oximeter. An example of an unfiltered pulse density signal captured by a photoplethysmograph is shown in FIG. 12A.

The processor 215 receives the data signal from the sensor 213 and reduces or processes the data signal into at least one output 220 by at least calculating a variation of the data signal across the respiration periods over which data were collected. In an example, the processor 215 applies a first filter to obtain the respiration signal and a second filter to obtain the cardiac pulse signal.

As shown in FIG. 8, the system 200 also has a signal conditioning module 250 that includes an amplifier 252 and an analog-to-digital converter 254. The steps carried out by the signal conditioning module 250 are set forth in FIG. 9. The signal conditioning module 250 captures the pulse density signal from the sensor 213. The signal is amplified via hardware or software as shown in step 310 of FIG. 9. The signal is converted from a continuous analog signal to a series of digital values per a defined sampling rate as shown in step 320. The sampling rate of the converter 254 translates the data signal to a series of digital values over time. The higher the sampling rate, the more precise the resolution and exactness of the digital representation of the analog waveform. The converted signal is then inverted as shown in step 330 because an increase in pulse density that corresponds to an increase in pulsatile strength corresponds to an increased amount of absorbed light and a smaller corresponding value through the skin. The signal is inverted so that the increased absorption and corresponding increase in blood density appear in an upward or positive direction. As shown in step 340, the inverted signal is then transmitted via either a hardwired circuit or wirelessly to a remote receiver for further processing.

The system 200 also has a signal processing module 260 that is configured to receive and filter the converted signal to identify each respiration sampling period and the plurality of cardiac cycles occurring during each respiration sampling period. The steps carried out by the signal processing module 260 are set forth in FIG. 10. The converted pulse density signal is received from the signal conditioning module, as shown in step 410. A band pass filter is applied to the signal to capture the respiratory signal, as shown in step 420. The process of respiration increases chest pressure during inspiration and reduces it during exhalation, thereby creating a modulating effect on the cardiac measures. In spontaneously breathing patients, the erratic nature of breathing cycles creates undesirable variability in the pulse density signal due to this modulating effect. The effects of spontaneous breathing are addressed by obtaining the mean of these derived values over each respiration sampling period in order to remove this modulating effect. In an example, respiration sampling periods are identified by filtering the inverted pulse density signal into frequency bands of possible respiration frequencies. In an example, the following bands are used: 0.12 to 0.28 Hz; 0.16 to 0.32 Hz; 0.20 to 0.36 Hz; 0.24 to 0.40 Hz; and 0.28 to 0.44 Hz. Next, an algorithm, such as a power analysis, is applied to each band in order to identify which band is the strongest (i.e., has the highest dB) in order to select the optimum respiration frequency range. See step 425. Next, a maximum detection algorithm is applied to the optimum respiration frequency range to identify respiration period start and end sampling points that correspond to the selected respiration sampling period. See step 435. FIG. 12B shows the filtered respiration sampling period derived from the pulse density signal shown in FIG. 12A. In another embodiment, respiration frequency is obtained via wavelet analysis. Wavelet analysis is useful where the pulse density signal is obtained from a population where the frequency is more variable, such as from a mobile population.

Figure 12C:
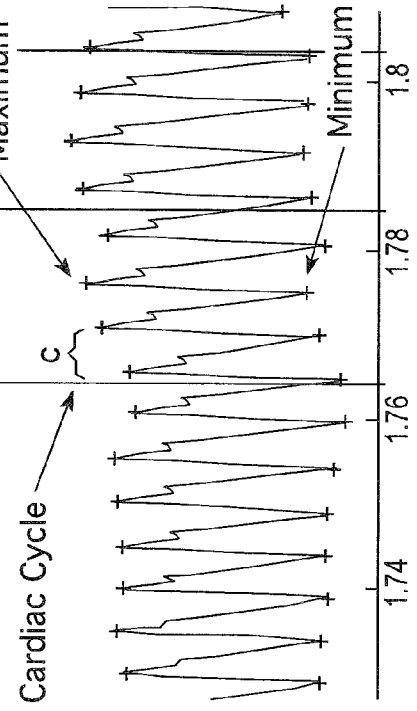
FIG. 12C shows the pulse density signal of FIG. 12A filtered to capture a plurality of cardiac cycles occurring during each of the respiration sampling periods shown in FIG. 12B.

The signal processing module 260 also identifies cardiac cycles that occur during each respiration sampling period. Cardiac cycles are identified by applying a low pass filter to the converted signal in order to obtain a cardiac pulse waveform, as shown in step 440. In an example, the filter range is 2.3 to 0.8 Hz, although other ranges may be appropriate depending upon the intended use population (i.e., infants and trauma patients may require higher ranges). In another example, wavelet analysis is used to define the optimum cardiac frequency. Next, a peak and valley detection algorithm is applied to the cardiac pulse waveform to identify the minimum and maximum values. Pulse pressure for each cardiac cycle is calculated by subtracting the minimum pressure of the filtered cardiac pulse for the cardiac cycle within a respiration sampling period from the maximum pressure of the filtered cardiac pulse waveform for that cardiac cycle. The mean pulse pressure value for each cardiac cycle is calculated according to Equation 3 (below). The signal processing module also calculates the mean minimum pressure for each respiration sampling period according to Equation 6 (below) and the peak blood flow velocity for each respiration sampling period according to Equation 5 (below). FIG. 12C shows the filtered cardiac pulse signal and the cardiac cycles derived from the pulse density signal shown in FIG. 12A.

Figure 11A:
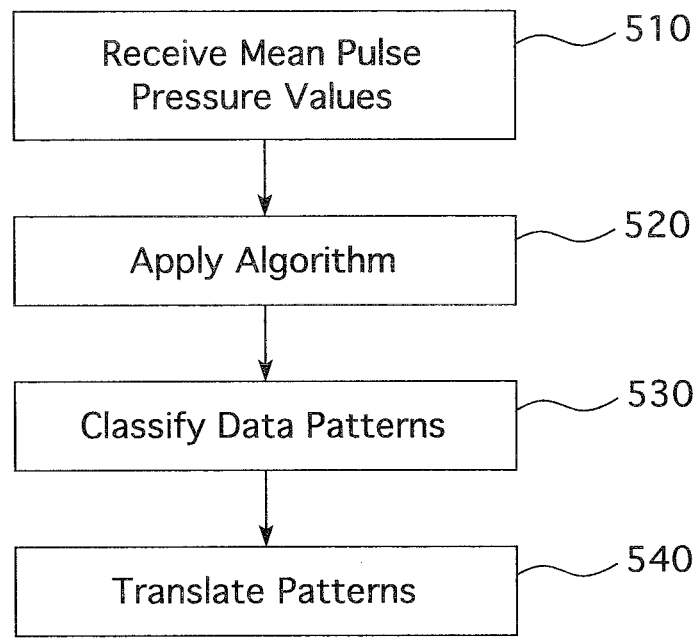
FIG. 11 shows a flow diagram outlining the steps performed by the pattern recognition module.

The system 200 also has a pattern recognition module 270 that is configured to calculate a change in peak blood flow velocity and a change in mean pulse pressure between two respiration sampling periods. The steps performed by the pattern recognition module 270 are shown in FIG. 11. The respiration sampling periods are optionally consecutive. As shown in FIG. 11A, the pattern recognition module 270 receives the mean pulse pressure values for each respiration sampling period from the signal processing module 260. See step 510. In order to assess a time series of mean pulse pressure values, as shown in step 520, an algorithm is applied to each consecutive mean pulse pressure value to calculate an absolute or a relative change in mean pulse pressure between two respiration sampling periods. In an example, an absolute change in mean pulse pressure between two respiration sampling periods is calculated. In another example, a relative change in mean pulse pressure between two respiration sampling periods is calculated, such as percent change of the peak amplitude, or the percentage change in the average or root-mean-square given the oscillating nature of the mean pulse pressure. The algorithm removes outlier mean pulse pressure values to account for unplanned or physiological artifacts (i.e., coughing, moving, etc). The pattern recognition module 270 classifies the change in mean pulse pressure into a classification system. See step 530. The classified change in mean pulse pressure is then translated into a graphic such as a gauge or a set of textually defined conditions to identify the volume status of the patient, such as to determine if the patient has a volume deficiency, as shown in step 540. Optionally, the translation is entered into a database or file as part of the patient record.

Figure 11B:
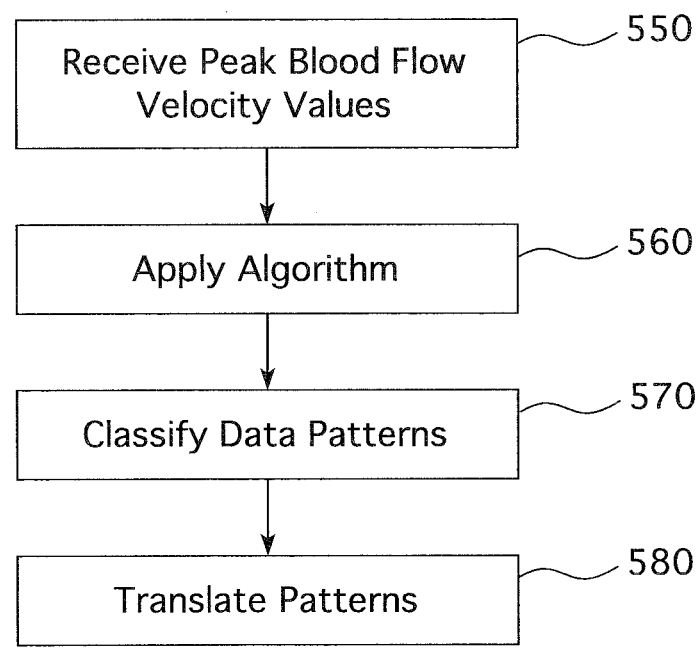

As shown in FIG. 11B, the pattern recognition module 270 also receives the peak blood flow velocity values for each respiration sampling period from the signal processing module 260. See step 550. In order to assess a time series of peak blood flow velocity values, as shown in step 560, an algorithm is applied to each consecutive peak blood flow velocity value to calculate an absolute or a relative change in peak blood flow velocity between two respiration sampling periods. In an example, an absolute change in peak blood flow velocity between two respiration sampling periods is calculated. In another example, a relative change in peak blood flow velocity between two respiration sampling periods is calculated, such as percent change of the peak amplitude average or root-mean-square given the oscillating nature of the mean pulse pressure. The algorithm removes outlier peak blood flow velocity values to account for unplanned or physiological artifacts (i.e., coughing, moving, etc). The pattern recognition module 270 classifies the change in peak blood flow velocity into a classification system, as shown in step 570. The classified change in peak blood flow velocity is then translated into a graphic such as a gauge or a set of textually defined conditions to identify the volume status of the patient, such as to determine if the patient has a volume deficiency. See step 580. Optionally, the translation is entered into a database or file as part of the patient record.

The systems 100, 200 may further include a mass storage device, peripheral devices, portable storage medium drives, input control device, a graphics subsystem, and an output display (not shown). The systems 100, 200 may be connected through one or more data communications means. For example, the processor and the main memory may be connected via a local microprocessor bus, and the mass storage device, peripheral devices, portable storage medium drives, graphics subsystem may be connected via one or more input/output (I/O) busses. The mass storage device, which may be implemented with a magnetic disk drive or an optical disk drive, is a non-volatile storage device for storing data and instructions for use by the processor. In the software embodiment, the mass storage device stores the information software for loading to the main memory.

Figure 2A:
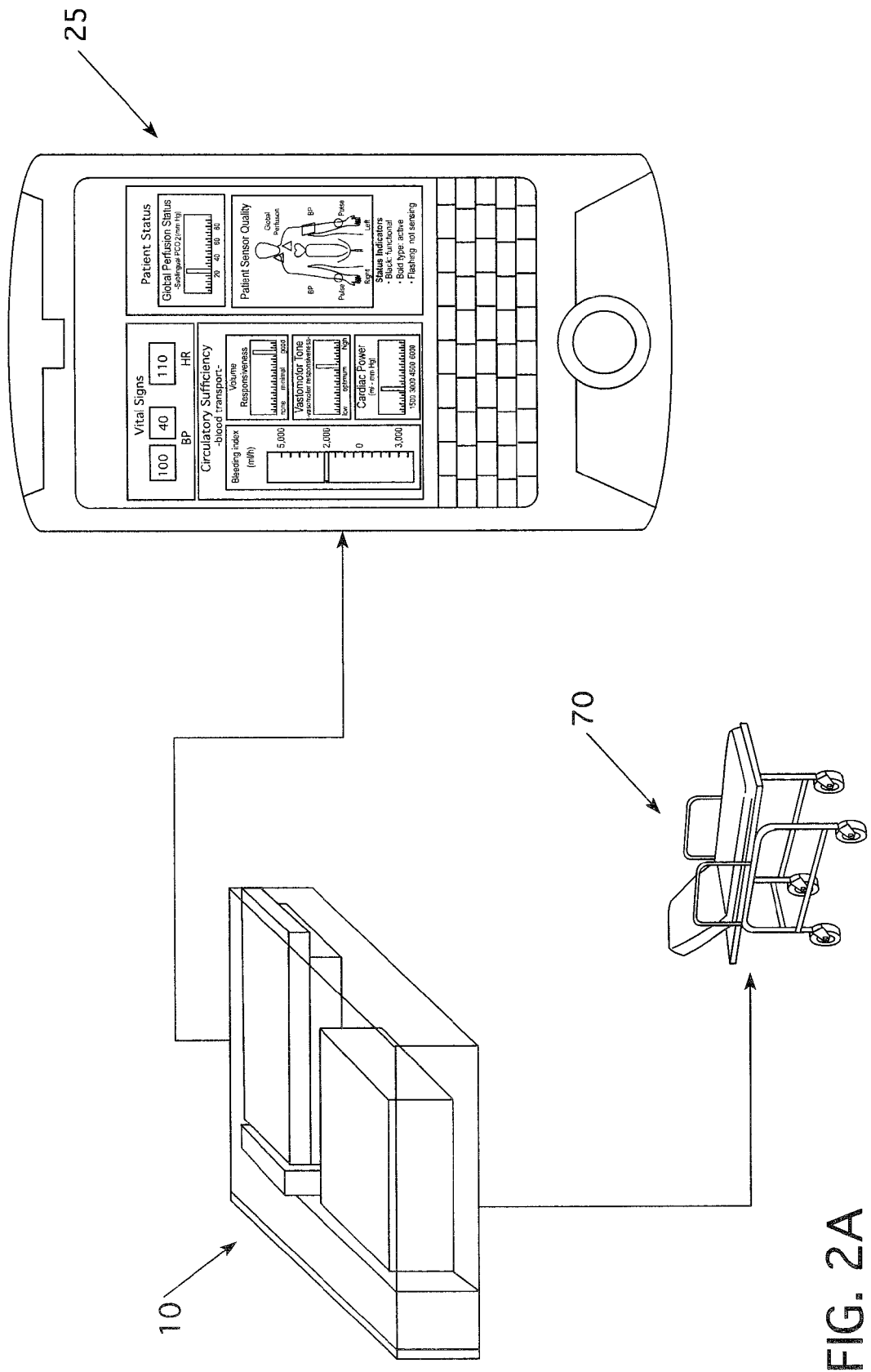
FIG. 2 shows schematics of examples of embodiments of the device of the claimed invention. In the example shown in FIG. 2A, the claimed device is shown in conjunction with a hospital bed. In the example shown in FIG. 2B, the claimed device is shown wrapped around a subject's leg.
Figure 2B:
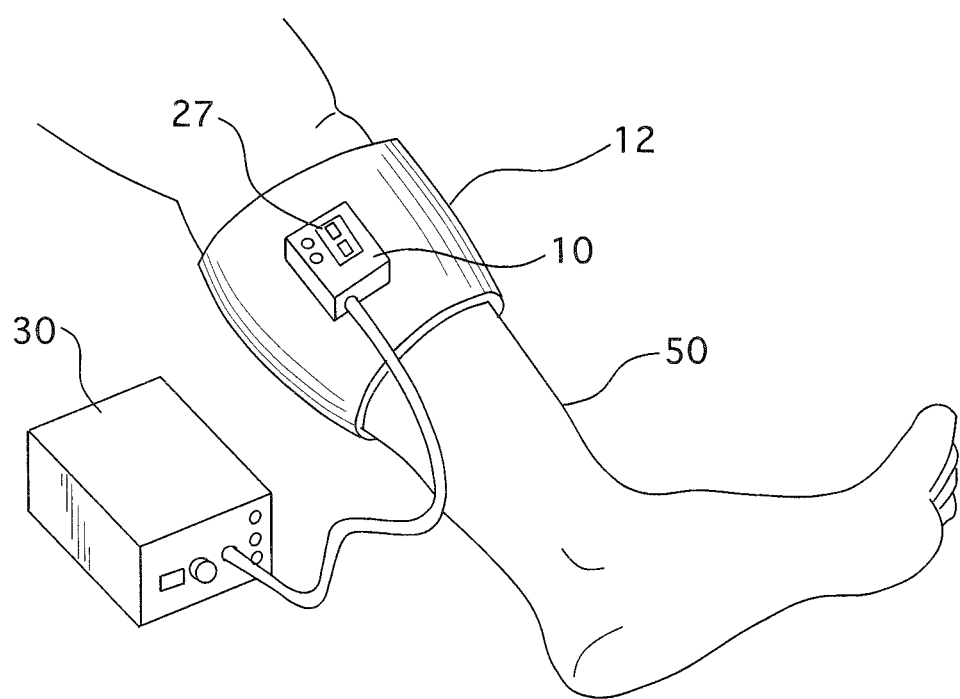
Figure 3:
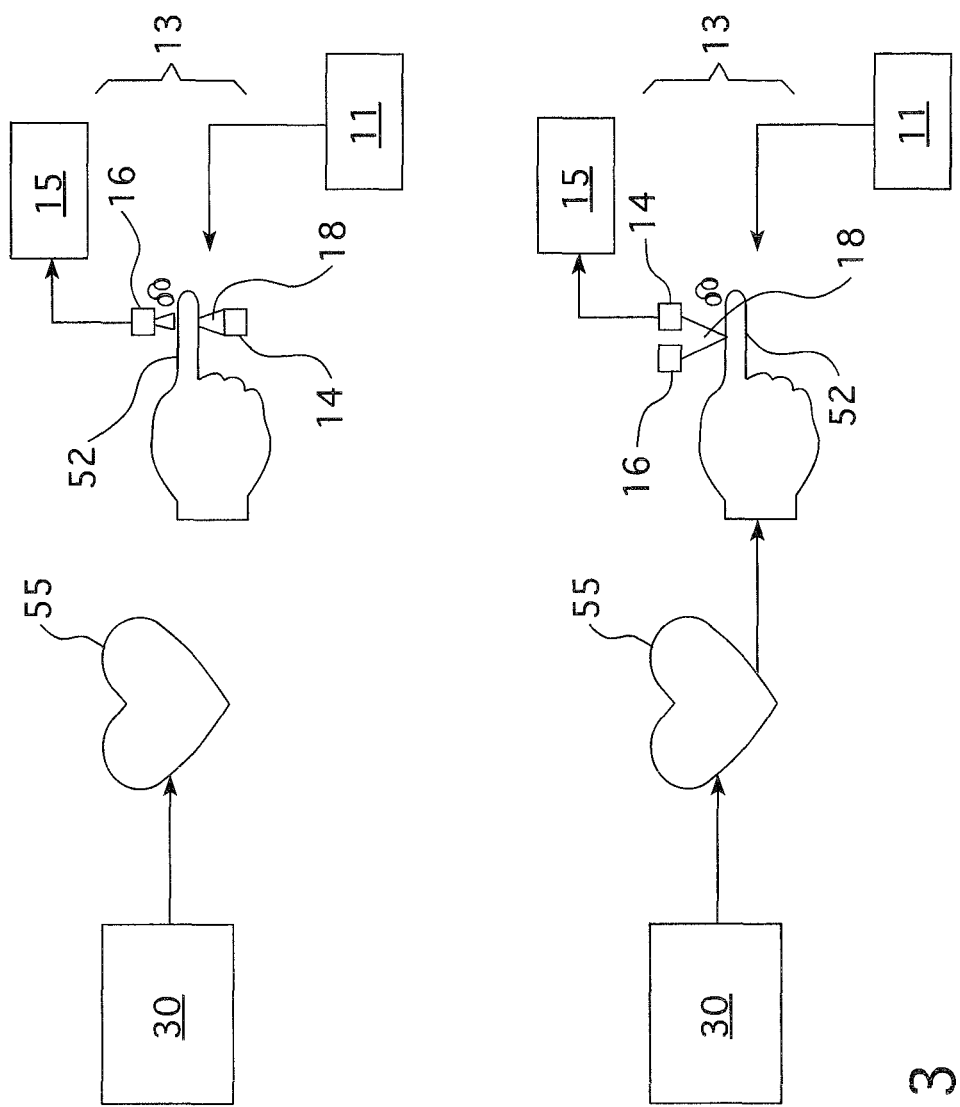
FIG. 3 shows schematics of an example of the claimed device.

FIGS. 2 and 3 show schematics of embodiments of the claimed device 10. In an example, device 10 is portable such that device 10 may be carried into challenging settings outside of the hospital such as in far forward military applications, in ambulances, and/or by emergency response personnel. In examples, device 10 may be attached to a hospital bed 70 (see FIG. 2A), a gurney (not shown), a wheelchair (not shown), or a part of the subject's 50 body (see FIG. 2B, described in greater detail below). As shown in the figures, and referring particularly to FIGS. 2-3, the claimed device 10 is comprised of a controller or a control 11, a sensor 13, and a processor 15. The controller 11 initiates collection of a plurality of data related to a physiological condition. In an example, the physiological condition is related to the subject's 50 cardiovascular system or is indicative of dysfunction of the subject's 50 cardiovascular system, either directly or indirectly, such as is illustrated in the chart recordings and graph shown in FIG. 1. In this way, collected data related to the physiological condition provide an indirect index of cardiovascular dysfunction such that relative changes in the physiological condition may indicate cardiovascular dysfunction.

In examples, the controller 11 is a switch or a trigger that initiates data collection by the sensor 13, 213 and that may be operated manually, automatically, or both. In another example, the controller 11 is a plurality of software rules that manage the data collection process. In another example, the controller 11 is a combination of the software rules and at least one of the switches.

The sensor 13, 213 continuously collects data over a plurality of cycles 80 (see FIG. 7) or over a respiratory sampling range R(Y) (see FIG. 12). In an example, there is also a plurality of subcycles 85 within each cycle 80 or a plurality of cardiac cycles "c" occurring during each respiratory sampling range R(Y). In the example shown in FIG. 7, cycles 80 are respiratory cycles. Sensor 13, 213 transfers or transmits data to the processor 15, 215. Sensor 13, 213 may be any component that is capable of converting energy into a useable physiological signal. In examples, sensor 13, 213 is comprised of analog-to-digital converter processing and algorithms to convert energy into a usable physiological signal, such as for example the measure of oxygenated hemoglobin as represented by a pulse pressure chart recording of pulse oximeter density (see FIGS. 1A and 1B). In examples, the sensor 13, 213 is a photoplethysmograph (see FIG. 3) that utilizes either absorbed (FIG. 3A) or reflected (FIG. 3B) light waves. Other examples of sensors 13, 213 include impedance cardiographs, ultra wide-band radar, esophageal pulse Doppler, or thermodilution. This list is not intended to be limiting however, and sensor 13, 213 may include any component that does not interfere with the intended purpose of the claimed system.

The processor 15 receives the data signal from the sensor 13 and reduces or processes the data signal into at least one output 20 by at least calculating a variation of the data signal across the cycles over which data were collected. In an example, the processor 15 applies a filter to capture the maximum and minimum data signal in each subcycle 85 to assess and treat cardiovascularly unstable patients 85 and the mean of the maximum data signals and minimum data signals across all cycles 80, and uses a formula to calculate the deviation of the signal across all cycles 80. The use of this formula imparts on the device 10 a level of sensitivity to detect change in the physiologic condition previously unavailable to non-invasive devices.

In an example, the formula is embodied in software rules. In one embodiment, the formula is as follows:

$$\text{percent deviation}_{data\ signal} = (P\text{mean}_{max} - P\text{mean}_{min}) / [(P\text{mean}_{max} + P\text{mean}_{min})/2] \times 100.$$ [Equation 1]

In this formula, percent deviation$_{data\ signal}$ is a variation in a data signal received from the sensor 13. Pmean$_{max}$ is a maximum mean value of the data signal across the plurality of cycles 80, and Pmean$_{min}$ is a minimum mean value of the data signal across the cycles 80. A mean value of the data signal is calculated for each subcycle (c) 85 as follows:

$$P\text{mean}_c = P\text{max}_c + P\text{min}_c / 2.$$ [Equation 2]

Figure 7:
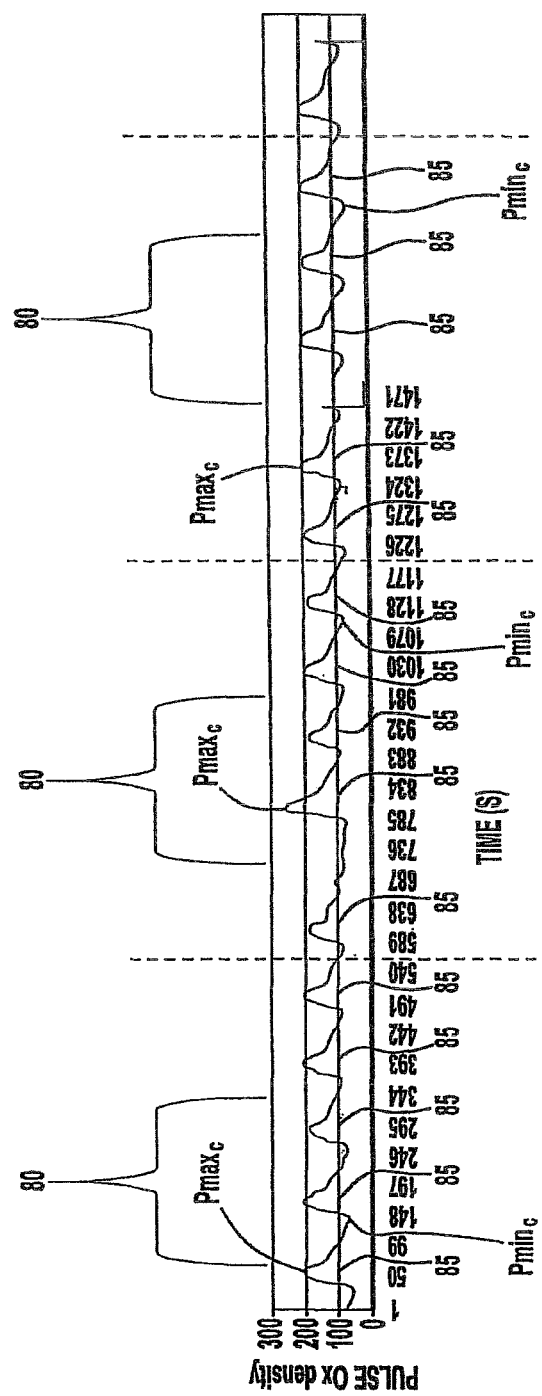
FIG. 7 shows a chart recording of pulse oximeter density collected during a perturbation.

In this formula, and referring to the example chart recording shown in FIG. 7, Pmax$_c$ is the maximum data signal in a given subcycle (c) and Pmin$_c$ is the minimum data signal in a given subcycle (c). Pmean$_{max}$ and Pmean$_{min}$ are the highest and lowest mean value of the data signal, respectively, out of all of the Pmean$_c$ calculated (i.e., one Pmean$_c$ for each of the subcycles (c)).

In another embodiment, volume status of a patient is identified by calculating a change in mean pulse pressure between two respiration sampling periods R(Y), R(Y+1). In an example, a positive change in mean pulse pressure between two respiration sampling periods indicates that the patient is volume insufficient. Optionally, the respiration sampling periods R(Y), R(Y+1) are consecutive. Mean pulse pressure for a respiration sampling period (PPmean$_{R(Y)}$) is calculated as the quotient of the sum of the pulse pressure for each cardiac cycle occurring during the respiration sampling period to the total number of cardiac cycles occurring during the respiration sampling period and is used as an index of a patient's volume status. The formula for calculating mean pulse pressure for a respiration sampling period R(Y) having x cardiac cycles is:

$$PP\text{mean}_{R(Y)} = ((P\text{max}_{1R(Y)} - P\text{min}_{1R(Y)}) + \ldots + (P\text{max}_{xR(Y)} - P\text{min}_{xR(Y)}))/x,$$ [Equation 3]

where Pmax$_{1R(Y)}$ is the maximum pressure of the filtered cardiac signal for the first cardiac cycle within the respiration sampling period R(Y), where Pmin$_{1R(Y)}$ is the minimum pressure of the filtered cardiac signal for the first cardiac cycle within the respiration sampling period R(Y), where Pmax$_{xR(Y)}$ is the maximum pressure of the filtered cardiac signal for the last cardiac cycle within the respiration sampling period R(Y), and where Pmin$_{xR(Y)}$ is the minimum pressure of the filtered cardiac signal for the last cardiac cycle within the respiration sampling period R(Y).

The change in mean pulse pressure between two respiration sampling periods R(Y) and R(Y+1) is calculated as follows:

$$\Delta PP\text{mean} = (PP\text{mean}_{R(Y+1)} - PP\text{mean}_{R(Y)}) / (PP\text{mean}_{R(Y+1)} + PP\text{mean}_{R(Y)}).$$ [Equation 4]

In another embodiment, peak blood flow velocity is used as an index of a patient's volume status. In another embodiment, volume status of a patient is identified by calculating a change in peak blood flow velocity between two respiration sampling periods. Optionally, the respiration sampling periods are consecutive. In an example, a positive change in peak blood flow velocity between two respiration sampling periods indicates that the patient is volume insufficient. Peak blood flow velocity for a respiration sampling period (PBFV) is calculated as the difference between a mean minimum pressure for the respiration sampling period and a mean pulse pressure for the respiration sampling period. The formula for calculating peak blood flow velocity for a respiration sampling period R(Y) is:

$$PBFV = P\text{min(mean)}_{R(Y)} - PP\text{mean}_{R(Y)},$$ [Equation 5]

where Pmin(mean)$_{R(Y)}$ is the mean minimum pressure for the respiration sampling period and is calculated as the quotient of the sum of the minimum pressure for each cardiac cycle occurring during the respiration sampling period to the total number of cardiac cycles x occurring during the respiration sampling period R(Y), calculated as:

$$P\text{min(mean)}_{R(Y)} = (P\text{min}_{1R(Y)} + \ldots + P\text{min}_{xR(Y)})/x,$$ [Equation 6]

where Pmim$_{1R(Y)}$ is the minimum pressure of the filtered cardiac signal for the first cardiac cycle within the respiration sampling period R(Y), and where Pmin$_{xR(Y)}$ is the minimum pressure of the filtered cardiac signal for the last cardiac cycle within the respiration sampling period R(Y).

While an embodiment of the present invention contemplates that the output 20, 220 is a percent deviation in the data signal, output 20, 220 may also be the plurality of data collected, the data signal itself, an information set, an interface, or a combination thereof. In other examples, output 20, 220 is an interpretation of data signal and may optionally suggest action or treatment protocols. Any output may be graphical, numerical, or textual.

Output 20, 220 may be displayed remotely, on the device itself, and/or may be integrated with an interface such as the one shown in FIG. 4 and described in detail below. In examples, the output 20, 220 is displayed on a handheld device, a monitor screen 25 (see FIG. 4), a display window 27 (see FIG. 2B), and/or any other display means known in the art that does not interfere with the intended use of the claimed device. As shown in the example in FIG. 4, output is displayed on a monitor 25 and is integrated with an interface system that provides, for example, subject-specific information such as direct cardiovascular measurements, analytics, sensor signal quality, and patient status. In an example, output 20, 220 is interpretations of gauges and measures that would enable a caregiver at any level of competency to interpret the analysis and to determine an appropriate action, such as treatment protocol. In an example, the interpretation indicates that the subject is deficient and the form of the deficiency related to norms. Other examples of information that may be displayed as part of the interface include biographical information about subject such as name, patient number, age, gender, medical history, and known allergies to pharmacological agents. In an example, the output 20, 220 is an objective directive for at least one proposed treatment protocol for treating the subject.

In an example, the device 10 of the claimed invention further comprises an activator 30, 230. In an example, the activator 30 perturbs the cardiovascular system of the subject 50 in order to assess the cardiovascular system's response (i.e., the percent deviation$_{data\ signal}$) to the perturbation and to use that response or percent deviation$_{data\ signal}$ to identify cardiovascular insufficiency. In other examples, mean pulse pressure or peak blood flow velocity are as indices of the volume status of a patient. In this way, in an example, the claimed device collects the data signal before, at the beginning of, and/or after the perturbation. In examples, the activator 30, 230 is administration of an agent, a physical maneuver, and/or mechanical ventilation of the subject. Where the activator 30, 230 is an agent, examples include but are not limited to administration of a bolus volume infusion or a pharmacologic agent such as a vasoconstrictor, a vasodilator, or a vasoactive agent, including for examples norepinephrine, epinephrine, and atropine. Where the activator 30, 230 is administering a physical maneuver, examples include but are not limited to raising a subject's leg about 30% from resting position, compression of a part of the subject's body, such as a calf (see compression device shown in FIG. 2B and described below) or the abdomen, the Valsalva maneuver, or a change in physical position of the subject, such as going from a sitting to a standing position. The activator 30, 230 may be activated by an automatic or manual switch or trigger, or by a motion sensor to recognize physical maneuvers.

In the example shown in FIG. 2A, the device 10 is portable and may be attached to a hospital bed 70. The device 10 (i.e., the controller 11, the sensor 13, and the processor 15) is embodied within a small box, and in an example, the activator 30 and the output display, shown here as a monitor 25, are embodied within the same box. In other examples, the activator 30 and/or output display are remote.

In the example shown in FIG. 2B, the device 10 is an inflatable cuff 12 that may be worn around the subject's calf. In an example, an automated or manual controller 11 initiates collection of data by the sensor 13 continuously over a plurality of cycles 80. The sensor transfers 13 the data to the processor 15 as a data signal and the processor 15 reduces the data signal into at least one output, as described above. In an example, an activator 30 inflates the cuff 12 (i.e., a cardiovascular perturbation) such that the inflation causes an intravascular volume load equivalent to a change of approximately 300 mL of volume in the subject's cardiovascular system. The percent deviation$_{data\ signal}$, mean pulse pressure, or peak blood flow velocity are calculated by the processor 15 in response to the perturbation as described above. As shown in the example in FIG. 2B, the activator 30 is remotely connected to the device 10 by wired or wireless communication.

In another example, the activator is not remote (not shown). In this example, the output display is a display window 27.

Another schematic of an example of the claimed device 10 is shown in FIG. 3. In this example, the sensor 13 is a photoplethysmographic device comprised of a photosource 14 and a photodetector 16. A controller 11 initiates collection of pulse oximeter density, which is a measure of the amount of oxygenated hemoglobin present in the subject's blood. The activator 30 perturbs the cardiovascular system 55. The photosource 14 emits light waves 18 of a known wavelength that pass through the vascular bed of a part of the subject's body such as a fingertip 52, as shown in FIG. 3A. As shown in FIG. 3B, in another example light waves are reflected off a surface of the fingertip 52. The photodetector 16 measures the amount of oxygenated hemoglobin in the subject's blood over the plurality of cycles 80.

Figure 5A:
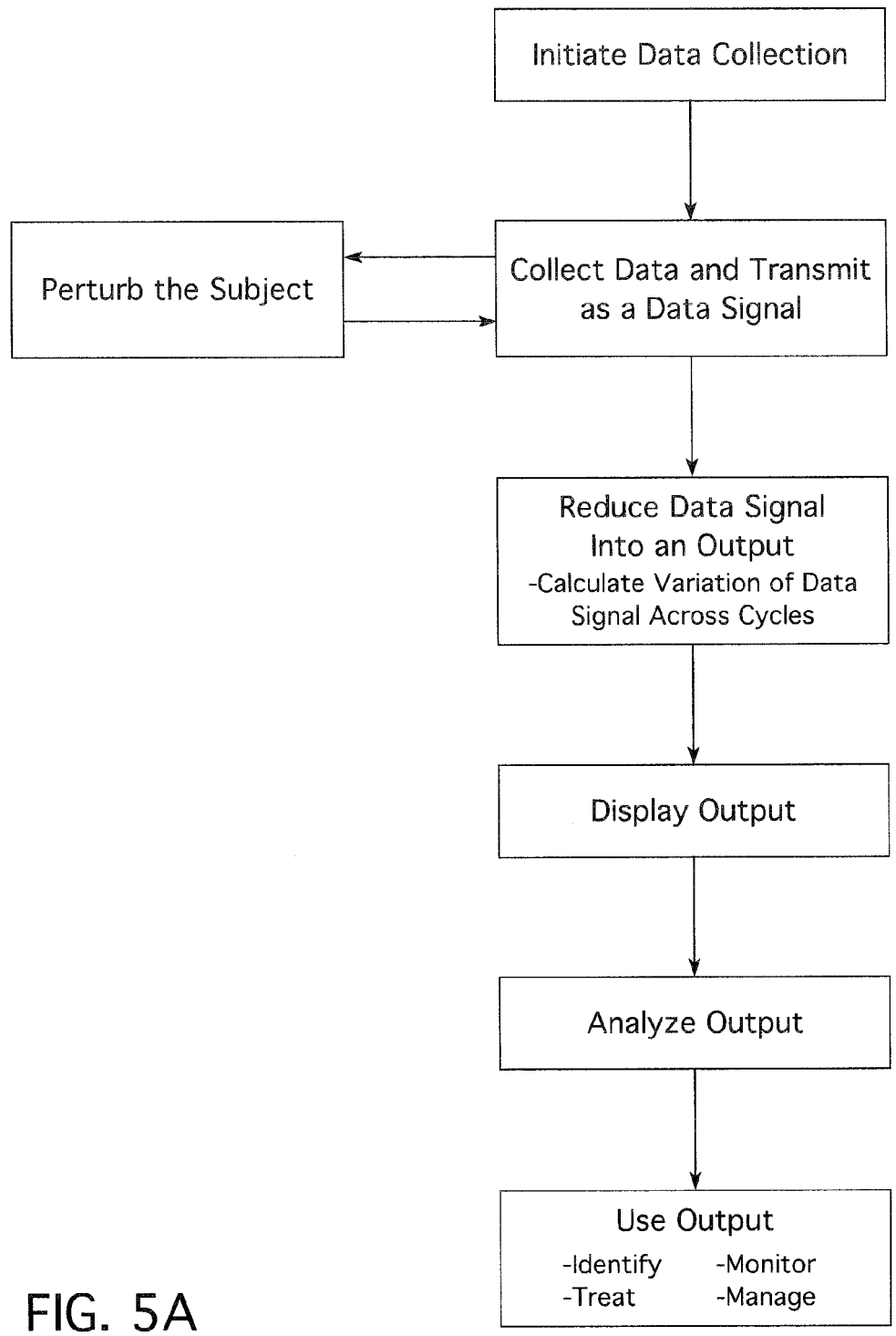
FIG. 5A and 5B show schematics outlining the steps of an example of a method using the device of the claimed invention.

In an embodiment, the claimed method uses the device 10 described above to identify cardiovascular insufficiency of a subject 50. In other examples, the claimed device is used to monitor a subject 50 (remotely or non-remotely), identify when the subject is hypovolemic or dehydrated (i.e., has decreased circulatory blood volume), manage a subject 50, and/or to institute a treatment protocol. Examples of use are provided in detail below. A schematic outlining the steps of an example of the claimed invention is depicted in FIG. 5.

In an example, the claimed method comprises the first step of initiating the collection of a plurality of data. In an example, data relate to a physiological condition of the subject 50, as described above. Data collection may be initiated by the controller 11 described above. In the example shown in FIG. 5, data collection need only be initiated one time because collection occurs continuously over the plurality of cycles 80. In other examples, such as where initiation is manually driven, the step of initiating data collection will be required every time data collection is desired or required.

The claimed method also comprises the step of collecting data. Collection is made by a sensor 13 such as the one described above. Examples of cycles 80 and subcycles 85 are identified in the chart recording shown in FIG. 7. As shown, data are collected across a plurality of cycles 80, such as respiratory cycles, and across sub-cycles 85 within each cycle, such as cardiac cycles.

The claimed method also comprises the step of reducing the received data signal into output. In an example, data are collected and subsequently reduced before, at the initiation of, and/or after a perturbation (described below). The processor 15, 215 calculates at least a variation to generate an output and may make additional calculations. In the claimed method, the processor 15, 215 uses at least one of the formulae described above to process the data signal.

In a next step, the subject's cardiovascular system is perturbed, for example by an activator 30. In another example, a healthcare provider 90 or a researcher perturbs the subject's cardiovascular system by performing a physical maneuver on the patient or by instructing the subject to perform such a maneuver. In other examples, an agent such as a bolus volume load or a pharmacological agent is administered to the subject. Perturbations include but are not limited to those described above.

Figure 4:
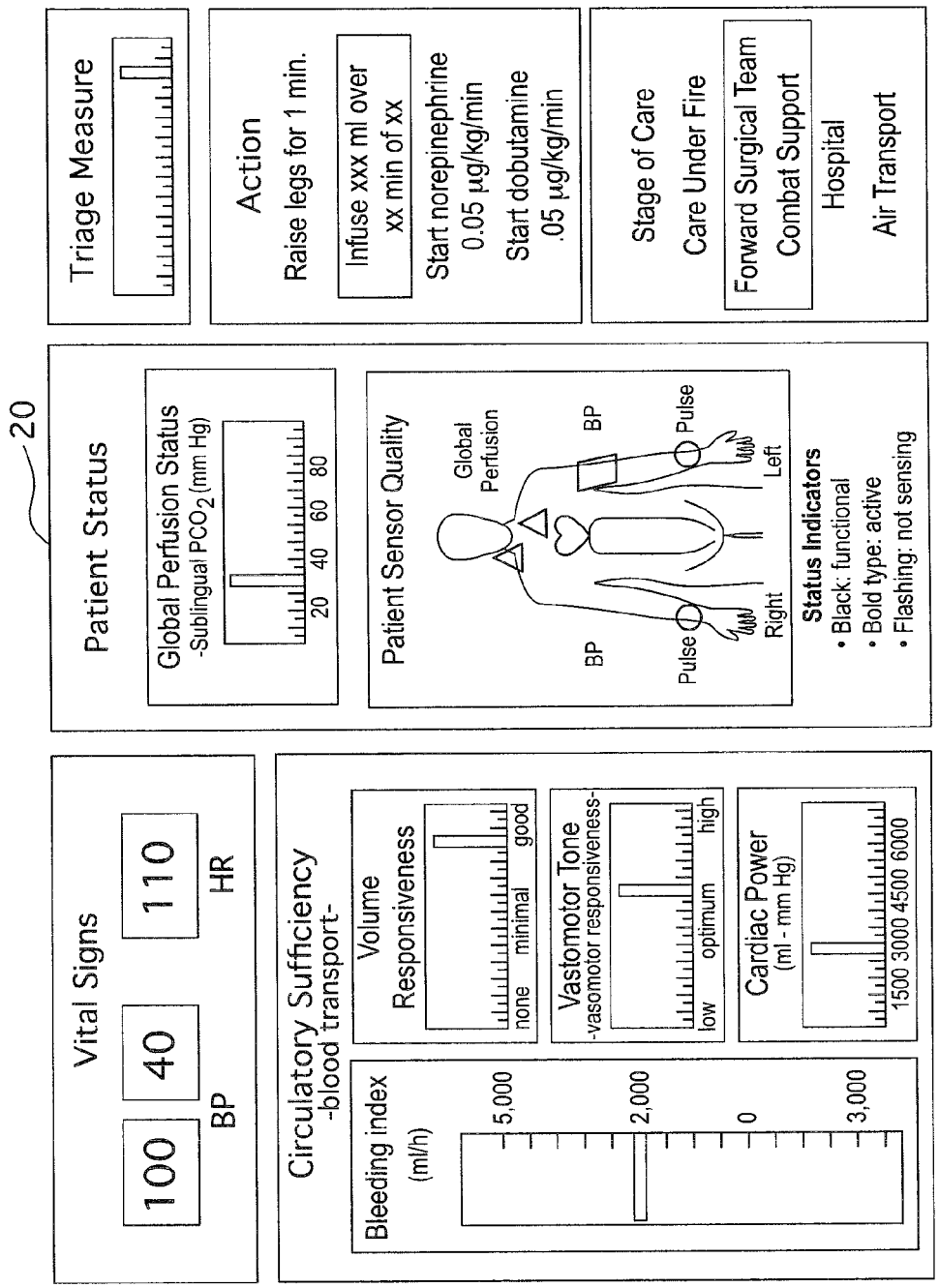
FIG. 4 shows an example of an embodiment of an output from the claimed device.

Referring still to FIG. 4, the next step of an example of a method of using the claimed invention is analyzing the output. In an example, the step of analyzing the data may be carried out by the processor 15 or by the healthcare provider 90 or both. For example, a physician treating the subject may analyze the data signal, and/or the calculations. In another example, the processor 15 analyzes the signal and sends graphics that portray analytics or trends, gauges or meters, alarms, or any combination thereof, to a display monitor. In another example, the processor 15 recommends a treatment protocol that suggests how subject 50 should be treated. This recommendation may be displayed on an output interface such as the one shown in FIG. 4. In examples, analysis comprises the steps of comparing data or calculations and deciding how to use the output.

Another step in an example of the claimed method is using the output to treat, monitor, or manage a subject 50, or to identify a physiological insufficiency in the subject, such as a cardiovascular insufficiency.

Figure 5B:
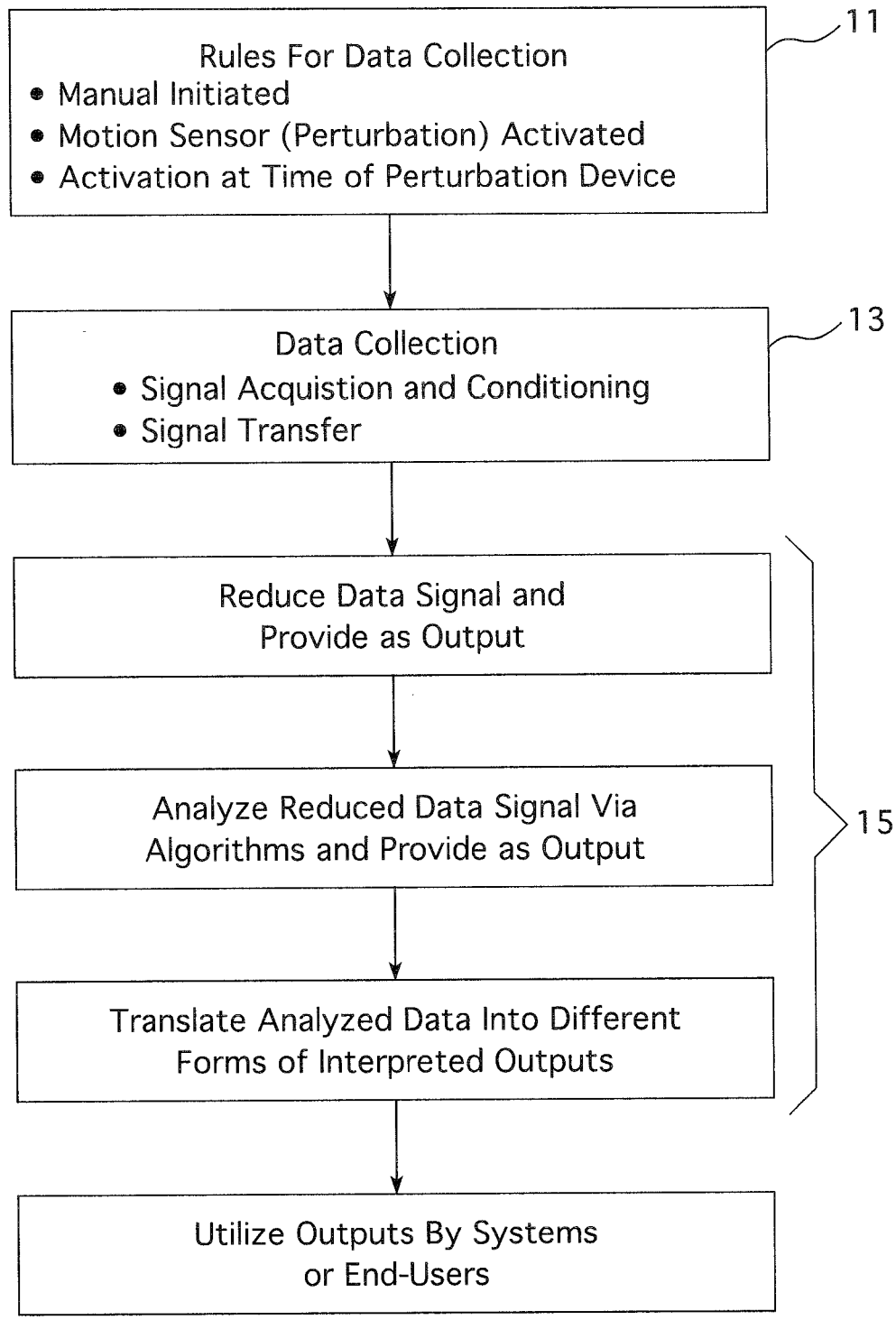

Another example of the method of using device 10 is shown in FIG. 5B. As shown, in a first step controller 11 operates using a set of rules. Controller 11 is manually initiated and a motion sensor is activated. Sensor 13 collects data and acquires and conditions the signal to be transferred to processor 15. Processor 15 reduces the signal such as by using at least one of the formulae described above and provides an output. In a next step, the analyzed signal is translated into any type of output, including the examples described above. The output is then used by a system or user, such as a physician 90, researcher, or leader.

Although the schematics in FIG. 5 show examples of the claimed method, the steps of the claimed method may be carried out in any order and may optionally be repeated at least one time.

EXAMPLES

The following examples are intended to illustrate the claimed invention and should not be construed as limiting the invention in any way.

Example 1

Unattended Monitoring in an Active Individual

A military war-fighter is in a combat situation in a hot, dry climate such as a desert. The war-fighter is clothed in a military combat uniform and is carrying on his back weapons and packs full of supplies and ammunition. He has not had fluids for more than three hours and is therefore susceptible to dehydration. The claimed device continuously and periodically monitors the soldier. The war-fighter is equipped with a motion sensor somewhere on his person that indicates when a physical motion has been performed initiating data collection. Either software rules applied to the motion sensor signal, software rules applied to the sensor, or a combination thereof provide a data quality indicator software bit to the device rules for when an ample physical motion provides an adequate perturbation to the cardiovascular system. Based on this quality indicator, the claimed continuously-monitoring device applies the classification algorithm to current sampled values of mean pulse pressure or peak blood flow velocity over five respiratory cycles in order to monitor the soldier's vascular volume. When the output from the claimed device indicates that the soldier is near or in a dehydrated or hypovolemic state, an alarm is initiated (e.g. a vibration, a sound, a light) to either alert the warfighter that he needs to rehydrate himself or is communicated to others.

The device may be similarly used in other situations in which individuals are subjected to extreme environments, such as fire-fighters and astronauts.

Example 2

Unattended or Attended Monitoring of an Immobile Patient

A patient afflicted with a chronic cardiovascular condition requires home healthcare where a telehomecare service is provided for remote caregiver monitoring. In another instance an individual has an acute cardiovascular condition and requires emergency medical technician assistance. The claimed device, such as the one shown in FIG. 3, is equipped with a compressible cuff (i.e. sequential compression device or SCD), commonly employed in hospitals to limit venous stasis to mimic the perturbation from passive leg raising) that the patient wears around his calf when in bed, on a stretcher or gurney such as the ones shown in FIG. 2B, above. The cuff is automatically inflated periodically to create a perturbation to the cardiovascular system. The device monitors oxygenated hemoglobin levels continuously over five respiratory cycles beginning at the point in time of the perturbation in order to monitor the change of pressure or volume of the vasculature and assessed for cardiovascular insufficiency and potentially contributions to cardiovascular insufficiency using the entire hemodynamic algorithm and additional devices (e.g. blood pressure). An output is continuously periodically updated with a current output every time the medical device performs a volume-loading perturbation followed by an assessment.

One form of the output could be a graphical display of a "patient dashboard" that provides interpreted results in easy-to-understand graphic metaphors such as a visual of a gauge or meter. This will allow caregivers of lesser competencies to apply complex hemodynamic concepts that indicate cardiovascular dysfunction such that more metabolically precise treatment protocols may be applied in a more responsive manner. Another output of the device may be an alarm of some type when the device has determined an extreme measure of cardiovascular dysfunction.

The output may be displayed at the bedside in the instance that the immobile patient is being attended to by a caregiver such as in an emergency transport. In addition or alternatively, the continually refreshed output may be transmitted via a wireless data communication, telecommunication, or satellite link to a remote location for continuous monitoring.

Example 3

Attended Immobile Patient Management

A hemodynamically unstable immobile critical care patient is being continuously monitored in a hospital acute care setting. The patient is spontaneously breathing making a mechanical ventilator unnecessary. A protocol is being administered to correct the patient's hemodynamic instability via a pharmacologic agent based protocol. The compressible cuff is worn around the patient's calf as in Example 2. In addition to a sensor to obtain a measure of the change in arterial pressure, cardiac output, or intravascular flow, other sensors are also captured such as measures of mean arterial pressure (i.e. an automated blood pressure cuff) to enable both output of all traditional vitals and analyses of the contributions of hemodynamic dysfunction such as disclosed in U.S. Pat. No. 6,776,764 to Pinsky. An output may be in the form of a patient dashboard at the bedside, communicated via a wireless communications method to caregiver's hand held device or to a clinical information system, or any combination. In this example the device is used for ongoing assessment of an instituted protocol to enable protocol optimization and responsive patient management.

Example 4

Peak Blood Flow Velocity vs. Peak Audio Doppler Recording

Figure 13:
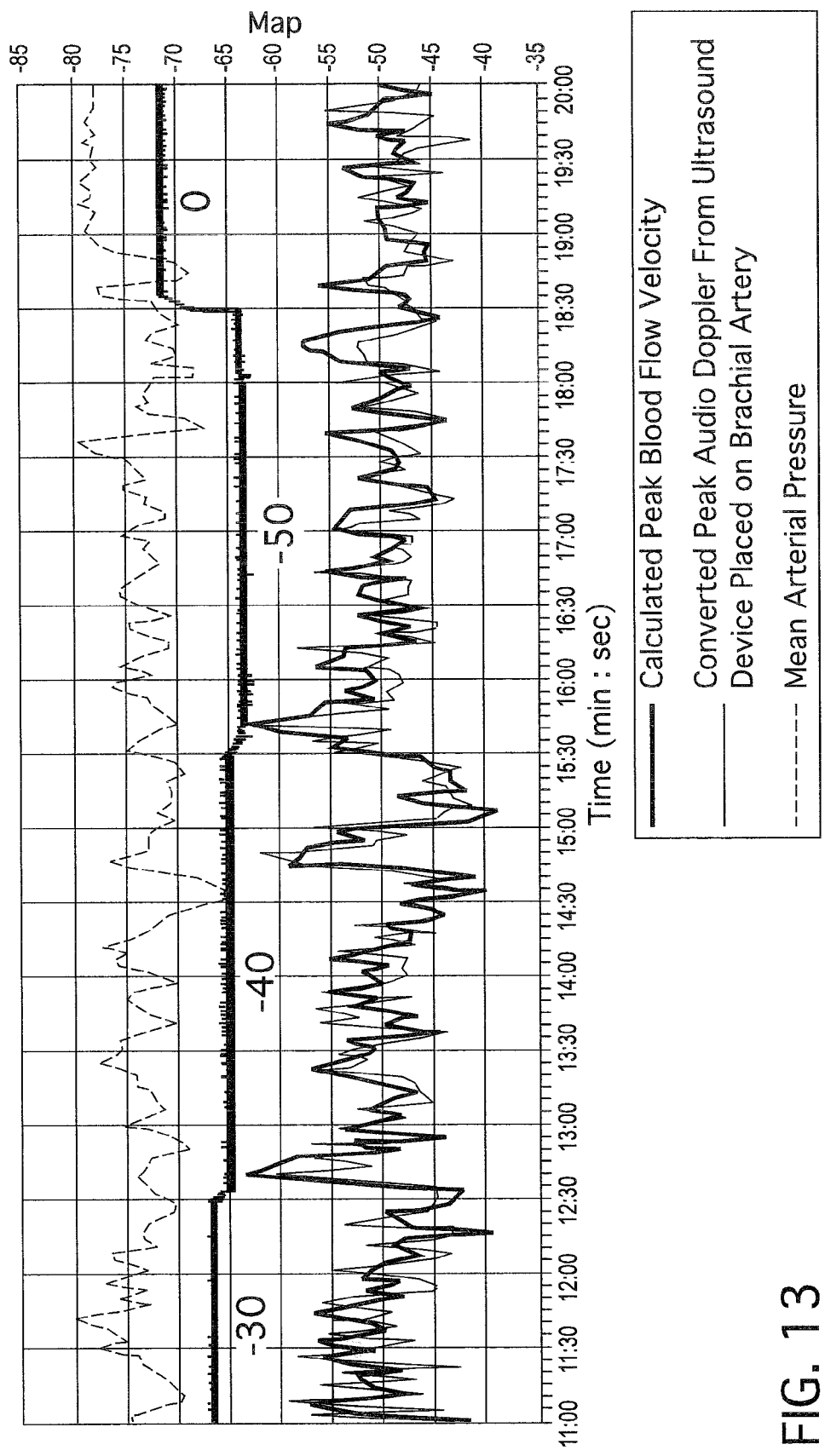
FIG. 13 shows the waveform from the derived peak blood flow velocity parameter superimposed on a waveform derived from the Doppler from an ultrasound device placed on the brachial artery.

FIG. 13 shows a calculated peak blood flow velocity waveform generated by the disclosed system and method. In this example, a patient was placed in a lower body negative pressure chamber that is used to simulate centralized hypovolemia.

The lower body negative pressure chamber consists of a sealed wooden box that encloses the lower body to above the hip (iliac crest). A neoprene wrap was place around the waist of the subject to ensure an adequate pressure seal. A vacuum was then operated continuously via a variable voltage control to adjust pressure in the chamber. A pressure transducer was attached via tygon tubing and calibrated to obtain current pressure in the chamber measured in mm of Hg. A protocol was employed of capturing baseline values and then to reduce pressure in 5 steps of −10 mm Hg holding each step for 3 minutes then releasing the pressure to return the chamber back to 0 mm Hg. The negative pressure sequesters blood to the lower extremities removing it from circulation. A decrease of 10 to 20 mm Hg has been shown to correlated to hemodynamic responses from a blood loss of 400 to 550 mL while a decrease of 20 to 40 mm Hg has been shown to correlate to a loss of 550 to 1,000 mL. The pulse density signal was recorded by a photoplethysmograph and was converted, inverted, and filtered as described above in order to generate the peak blood flow velocity waveform. Mean arterial pressure (MAP) was captured from a sensor placed on the finger using the volume clamp method (Finometer) to indicate how average pressure responds during controlled hypovolemia. As shown by FIG. 13, the peak blood flow velocity signal is superimposed on top of a converted peak audio Doppler recorded from an ultrasound device placed on a patient's brachial artery. These data confirm that the calculated peak blood flow velocity waveform correlates with the derived peak blood flow velocity. In both instances, an upward movement indicates an increased velocity. These changes correspond to the time course changes of the autoregulatory system. When the lower body negative pressure initially drops, there is a quick response from the baroreceptors that immediately sense changes in blood vessel pressure and activate a change in the compliance of the blood vessels causing the cardiac pulse wave to travel faster. After about 40 seconds to 1 minute, the cardiovascular system comes to a new steady state at which point it has adapted to the new level of blood loss. The cycle of immediate response and adaptation is evident at −30, −40, and again at −50 mm Hg.

Example 5

Volume Insufficiency Measurements

Figure 14:
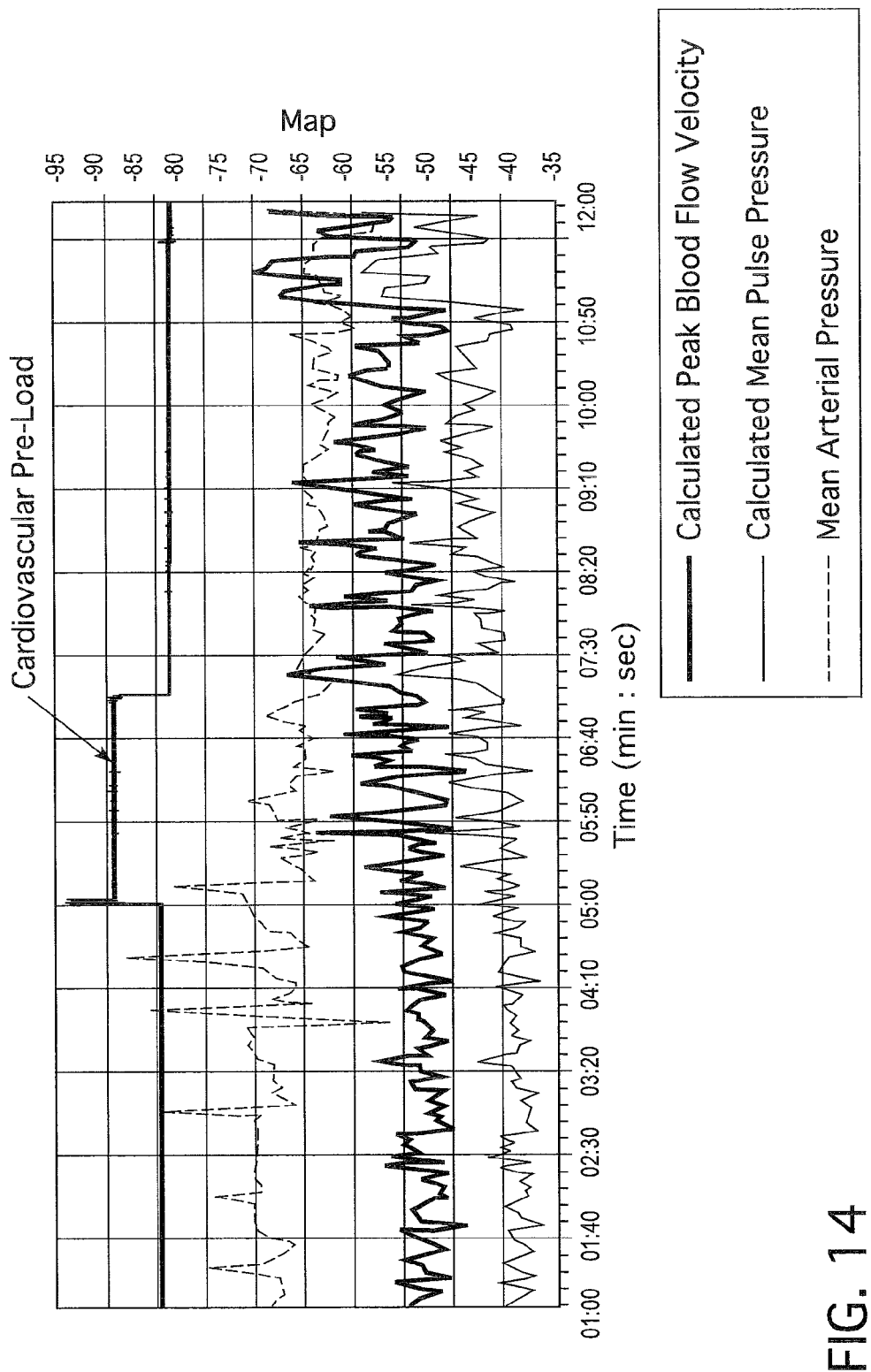
FIG. 14 shows the waveform from the derived mean pulse pressure parameter and the waveform from the derived peak blood flow velocity before, during, and after a cardiovascular pre-load is administered to a patient who is volume insufficient.

FIG. 14 shows a calculated peak blood flow velocity waveform generated by the disclosed system and method. In this example, the pulse density signal was recorded from a heart failure patient who was undergoing catheter laboratory testing. These data show what occurred in this patient in response to a passive leg raise used as the cardiovascular pre-load. The patient had not ingested any fluids since the evening before in preparation for the catheter lab testing and, as often the case, was dehydrated during testing. In this experiment, an accelerometer was placed on the patient's leg to indicate the initiation and conclusion of the passive leg raise (indicated as "Cardiovascular Pre-load" on FIG. 14).

The mean arterial pressure waveform was derived from a Finapres (Datex Ohmeda) device that employs a volume clamp method. A common artifact that occurs in the Finapres signal when a patient is volume insufficient (i.e., this patient was dehydrated) is a continual set of signal peaks as the volume clamp has little residual circulating volume in the finger to clamp down on as shown in FIG. 14 as "A." These peaks continue for approximately 30-40 seconds after the passive leg raise is performed, indicating the length of time required to affect the cardiovascular pre-load and resulting in a volume related change on the Starling curve. The additional circulating volume created by the leg raise provided this increased central venous return and cardiac pre-load effect.

The pulse density signal was recorded by a photoplethysmograph and was converted, inverted, and filtered as described above in order to generate the mean arterial pressure waveform and the peak blood flow velocity waveform. The increased cardiac pulse pressure is shown by the pulse pressure derived from the photoplethysmograph and is consistent with pulse pressure that could alternatively have been derived from an arterial pressure signal. Alternatively, studies have shown that an increase in the peak brachial blood flow velocity signal can also be used to identify volume insufficiency in response to a volume loading exercise. These data confirm this correlation.

Example 6

Recognizing a Patency or Stenosis

In end-stage renal disease, patients undergoing hemodialysis with long-term vascular access have an occlusion rate of 17-45% per year. Measured changes or ratios of elevated systolic velocity via Doppler ultrasound over time has been shown as a means to recognize changes in patency of a graft or fistula used as the access port for hemodialysis. Given that changes in peak blood flow velocity have been shown to correlate well to the peak Doppler ultrasound in Example 4, one example of use of the system is to measure this signal over time when placed on the finger or the arm where the access port is located.

While certain embodiments and applications have been described above, the skilled artisan will appreciate that there may be other applications to which the invention is well suited.

What is claimed is:

1. A computer-assisted method for identifying a volume status of a patient, the method comprising:
    administering a cardiovascular preload to the patient;
        continuously recording, prior to, during, and after the step of administering the cardiovascular preload to the patient, a pulse density signal from a non-invasive transducer transmitting data from the patient;
        applying, using a processor, a first filter to the pulse density signal to identify a first respiration sampling period recorded prior to the step of administering the cardiovascular preload and a second respiration sampling period recorded after the step of administering the cardiovascular preload;
        applying, using the processor, a second filter to the pulse density signal to identify a first plurality of cardiac cycles occurring during the first respiration sampling period and a second plurality of cardiac cycles occurring during the second respiration sampling period; and
        calculating, using the processor, a variation of the pulse density signal before and after the step of administering the cardiovascular preload, wherein the variation is used as an index of the volume status of the patient, wherein the variation is a quotient of a difference between a mean pulse density signal between the second and the first respiration sampling periods to a sum of the mean pulse density signal of the second and the first respiration sampling periods, wherein the mean pulse density signal for each respiration sampling period is a quotient of a sum of a difference between a maximum point on the pulse density signal and a minimum point on the pulse density signal for each cardiac cycle occurring during such respiration sampling period to a total number of cardiac cycles occurring during such respiration sampling period.

2. The method as in claim 1, further comprising calculating a peak blood flow velocity for at least one of the respiration sampling periods, wherein the peak blood flow velocity is a difference between a mean minimum point on the pulse density signal for the at least one of the respiration sampling periods and the mean pulse density signal for the at least one of the respiration sampling periods.

3. The method as in claim 2, further comprising calculating a change in peak blood flow velocity between the first and second respiration sampling periods.

4. The method as in claim 3, further comprising: classifying the change in peak blood flow velocity into a classification system; and translating the classified change in peak blood flow velocity to identify the volume status of the patient.

5. The method as in claim 1, further comprising: classifying the variation of the pulse density signal into a classification system; and translating the classified variation of the pulse density signal to identify the volume status of the patient.

6. The method as in claim 1, further comprising initiating a treatment protocol.

7. A system for identifying a volume status of a patient, the system comprising:
an activator that administers a cardiovascular preload to the patient;
a sensor that records a pulse density signal from a non-invasive transducer transmitting data from the patient prior to, during, and after the cardiovascular preload is administered to the patient;
a controller that controls the sensor to initiate the record of the pulse density signal;
a processor that is configured to: (i) apply a first filter to filter the pulse density signal to identify a first respiration sampling period and a second respiration sampling period, (ii) apply a second filter to filter the pulse density signal to identify a first plurality of cardiac cycles occurring during the first respiration sampling period and a second plurality of cardiac cycles occurring during the second respiration sampling period, and (iii) calculate a variation of the pulse density signal before and after the cardiovascular preload is administered to the patient, wherein the variation is used as an index of the volume status of the patient, wherein the variation is a quotient of a difference between a mean pulse density signal between the second and the first respiration sampling periods to a sum of the mean pulse density signal of the second and the first respiration sampling periods, wherein the mean pulse density signal for each respiration sampling period is a quotient of a sum of a difference between a maximum point on the pulse density signal and a minimum point on the pulse density signal for each cardiac cycle occurring during such respiration sampling period to a total number of cardiac cycles occurring during such respiration sampling period.

8. The system as in claim 7 wherein the processor is further configured to calculate a peak blood flow velocity for at least one of the respiration sampling periods, wherein the peak blood flow velocity is a difference between a mean minimum point on the pulse density signal for the at least one of the respiration sampling periods and the mean pulse density signal for the at least one of the respiration sampling periods.

9. The system as in claim 8 wherein the processor is further configured to calculate a change in peak blood flow velocity between the first and second respiration sampling periods.

10. The system as in claim 7 wherein the controller is selected from the group consisting of a manual switch, an automated switch, and software rules.

11. The system as in claim 7 wherein the sensor is a photoplethysmograph.

12. A system for identifying a volume status of a patient, the system comprising:
an activator that administers a cardiovascular preload to the patient;
a sensor that records a pulse density signal from a non-invasive transducer transmitting data from the patient prior to, during, and after the cardiovascular preload is administered to the patient;
a controller that controls the sensor to initiate the record of the pulse density signal;
a signal conditioning module comprising an amplifier that amplifies the pulse density signal and a converter that converts the amplified signal to a digital signal, the signal conditioning module being configured to transmit the converted, amplified signal;
a signal processing module configured to: (i) receive the converted, amplified signal from the signal conditioning module, (ii) apply a first filter to filter the signal to identify a first respiration sampling period and a second respiration sampling period, (iii) apply a second filter to filter the signal to identify a first plurality of cardiac cycles occurring during the first respiration sampling period and a second plurality of cardiac cycles occurring during the second respiration sampling period, and (iv) calculate a variation of the pulse density signal before and after the cardiovascular preload is administered to the patient, wherein the variation is used as an index of the volume status of the patient, wherein the variation is a quotient of a difference between a mean pulse density signal between the second and the first respiration sampling periods to a sum of the mean pulse density signal of the second and the first respiration sampling periods, wherein the mean pulse density signal for each respiration sampling period is a quotient of a sum of a difference between a maximum point on the pulse density signal and a minimum point on the pulse density signal for each cardiac cycle occurring during such respiration sampling period to a total number of cardiac cycles occurring during such respiration sampling period.

13. The system as in claim 12, further comprising a pattern recognition module configured to: (i) classify the variation in the pulse density signal into a classification system, and (ii) translate the classified variation in the pulse density signal to identify the volume status of the patient.

14. The system as in claim 12 wherein the signal processing module is further configured to calculate a peak blood flow velocity for at least one of the respiration sampling periods, wherein the peak blood flow velocity is a difference between a mean minimum point on the pulse density signal for the at least one of the respiration sampling periods and a mean pulse density signal for the at least one of the respiration sampling periods.

15. The system as in claim 14 further comprising a pattern recognition module configured to calculate a change in peak blood flow velocity between the first and second respiration sampling periods.

16. The system as in claim 15 wherein the pattern recognition module is further configured to: (i) classify the change in peak blood flow velocity into a classification system, and (ii) translate the classified change in peak blood flow velocity to identify the volume status of the patient.

17. A non-invasive apparatus configured to identify a volume status of a patient, the apparatus comprising:
- means for administering a cardiovascular preload to the patient
- means for recording a pulse density signal from a non-invasive transducer transmitting data from the patient prior to, during, and after administering the cardiovascular preload to the patient;
- means for applying a first filter to the pulse density signal to identify a first respiration sampling period recorded prior to the step of administering the cardiovascular preload and a second respiration sampling period recorded after the step of administering the cardiovascular preload;
- means for applying a second filter to the pulse density signal to identify a first plurality of cardiac cycles occurring during the first respiration sampling period and second plurality of cardiac cycles occurring during the second respiration sampling period; and
- means for calculating a variation of the pulse density signal before and after administering the cardiovascular preload, wherein the variation is used as an index of the volume status of the patient, wherein the variation is a quotient of a difference between a mean pulse density signal between the second and the first respiration sampling periods to a sum of the mean pulse density signal of the second and the first respiration sampling periods, wherein the mean pulse density signal for each respiration sampling period is a quotient of a sum of a difference between a maximum point on the pulse density signal and a minimum point on the pulse density signal for each cardiac cycle occurring during such respiration sampling period to a total number of cardiac cycles occurring during such respiration sampling period.

18. The apparatus as in claim 17 further comprising means for calculating a peak blood flow velocity for at least one of the respiration sampling periods, wherein the peak blood flow velocity is as a difference between a mean minimum point on the pulse density signal for the at least one of the respiration sampling periods and the mean pulse density signal for the at least one of the respiration sampling periods.

19. The apparatus as in claim 18 further comprising means for calculating a change in peak blood flow velocity between the first and second respiration sampling periods.

20. The apparatus as in claim 17 further comprising an output display.

21. The apparatus as in claim 17 wherein means for recording is a photoplethysmograph.

22. A computer-readable medium having stored therein instructions which, when executed by a processor, cause the processor to calculate a variation of a pulse density signal before and after administering a cardiovascular preload, wherein the variation is used as an index of the volume status of the patient, wherein the variation is a quotient of a difference between a mean pulse density signal between a second and a first respiration sampling period to a sum of the mean pulse density signal second and the first respiration sampling periods, wherein the mean pulse density signal for each respiration sampling period is a quotient of a sum of a difference between a maximum point on the pulse density signal and a minimum point on the pulse density signal for each cardiac cycle occurring during such respiration sampling period to a total number of cardiac cycles occurring during such respiration sampling period.

23. The computer-readable medium as in claim 22 having stored therein instructions which, when executed by the processor, cause the processor to calculate a peak blood flow velocity for at least one of the respiration sampling periods, wherein the peak blood flow velocity is a difference between a mean minimum signal for the at least one of the respiration sampling periods and the mean pulse density signal for the at least one of the respiration sampling periods.

24. The computer-readable medium as in claim 23 having stored therein instructions which, when executed by the processor, cause the processor to calculate a change in mean pulse pressure between the first and second respiration sampling periods.

25. The computer-readable medium as set forth in claim 22 having stored therein instructions which, when executed by the processor, cause the processor to generate an output.

* * * * *